United States Patent [19]
Shintani et al.

[11] Patent Number: 6,068,990

[45] Date of Patent: May 30, 2000

[54] PROTEINS, THEIR PRODUCTION AND USE

[75] Inventors: Yasushi Shintani; Kazunori Nishi, both of Tsukuba; Tomohiro Kawamoto, Osaka, all of Japan

[73] Assignee: Takeda Chemical Industries, Ltd., Osaka, Japan

[21] Appl. No.: 09/157,349

[22] Filed: Sep. 18, 1998

Related U.S. Application Data

[62] Division of application No. 08/835,099, Apr. 4, 1997, Pat. No. 5,874,277.

[30] Foreign Application Priority Data

May 4, 1996 [JP] Japan ................................. 8-083649

[51] Int. Cl.[7] .................................................. C12P 21/00
[52] U.S. Cl. ................. 435/69.1; 435/252.3; 435/320.1; 435/219; 435/226; 536/23.1; 536/23.5; 536/23.2; 530/350
[58] Field of Search ............................... 435/69.1, 252.3, 435/320.1, 219, 226; 536/23.1, 23.5, 23.2; 530/350

[56] References Cited

U.S. PATENT DOCUMENTS 5,874,277  2/1999  Shintani et al. ....................... 435/219

FOREIGN PATENT DOCUMENTS

WO 95/26506  10/1995  WIPO .
WO 95/33060  12/1995  WIPO .

OTHER PUBLICATIONS

Legendre et al. (1988) Inflammation 12/1, pp. 51–65.
Sorimachi et al. 1993) J. Biol. Chem. 90, pp. 19476–19482.
Database GenBank on STN, Accession No. A48764, Sorimachi et al.(1993).

Saito, et al., Proc. Natl. Acad. USA, vol. 90, (1993) pp. 2628–2632.
Sorimachi, et al., J. of Biol. Chem., vol. 90 (1993) pp. 19476–19482.
Legendre, et al., inflammation, vol. 12, No. 1, pp. 51–65 (1988).
Saido, et al., The FASEB Journal, vol. 8, pp. 814–822 (1994).

*Primary Examiner*—Karen Cochrane Carlson
*Assistant Examiner*—Enrique D. Longton
*Attorney, Agent, or Firm*—David G. Conlin; Cara Z. Lowen; Dike, Bronstein, Roberts & Cushman, LLP

[57] ABSTRACT

This invention relates to a novel calpain having a proteolytic activity, its partial peptide or a salt either of them, a DNA coding for the protein, a recombinant vector comprising the DNA, a transformant carrying the recombinant vector, a process for producing the protein, a pharmaceutical composition comprising the DNA, an antibody against the protein, a method for screening for a compound which activates or inhibits a proteolytic activity of the protein, a kit for screening for the compound, and a compound which activates or inhibits a proteolytic activity of the protein which is identified by the screening method or the kit. The DNA coding for the protein of the present invention can be used as a therapeutic and prophylactic composition for a variety of diseases including tumor, cerebral apoplexy, cerebral infarction, subarachnoid hemorrhage, Alzheimer's disease, myodystrophy, cataract, ischemic heart disease, atherosclerosis, arthritis, and collagen disease. Furthermore, the protein of the present invention is useful as a screening reagent for any compounds which activates or inhibits the function of the protein of the present invention. In addition, the antibody against the protein of the present invention specifically recognizes the protein of the present invention and can be used in the quantitative determination of the protein of the present invention in a test fluid.

5 Claims, 8 Drawing Sheets

```
CCGGGTTTTG CTGGAGTAGG GCCCCAACTC CTTGAAGCCC AGGGCCGAGG GGATGGCCGG    60
GAAGGACGGG TCCTGGAAGA GCGTCCCGGC CTCCAGGCAC TCGTTCCGCA GCGCCTCGTA   120
GTCCTGGTTG AGAGTCTCCA GGCTGGAGTG CAGTGGCAAG ATCTCGGCTC ACCGCAACCT   180
CTGCCTCCCA GGTTCCAGCG ATTCTCCTGC CTCAGCCTCC CAAGTAGCTG GGATTTCAGG   240
TGCCTGCCAC CATGCCCGGA CTCCTACAGG ACAACCAGGG ACAATCATCT TCACAGGAAC   300
CTATCCTCCC TGCTGGGTGG AAAGAGCATC GACCTGAGTC CAATCAGCTA CTTACAGGTC   360
AACTAAGAAG AGGACTGAGA GTTAACCATT GGATTGAGCA ACATCAAGAC CACCTGGATA   420
TTGGCCAATG GTTTTACCCT GACCATCTGC CAGAGGGAT GGAAATATGC ACCAAAACAT    480
TTCTGGCAGG AAAGGAGGCC CCTGTAACGA ATTGCCTTCT TCCTGCTCAG AGCCATGCCT   540
CCAATTCCTT GATGAATATT TGCTTCAAGC TGCACAATAA GCCTTCTCAT CTCAGTCA AT  600
                                                                Met
                                                                 1
GGG CTT GAA GCA AGA GCC CAC GGC CAT GGC AGC CCA GGC AGC TGG TGT     648
Gly Leu Lys Gln Glu Pro Thr Ala Met Ala Ala Gln Ala Ala Gly Val
      5                  10                  15

ATC TAG GCA GCG GGC AGC CAC TCA AGG TCT TGG CTC CAA CCA AAA CGC     696
Ser Arg Gln Arg Ala Ala Thr Gln Gly Leu Gly Ser Asn Gln Asn Ala
      20                  25                  30

TTT GAA GTA CTT GGG CCA GGA TTT CAA GAC CCT GAG GCA ACA GTG CTT     744
Leu Lys Tyr Leu Gly Gln Asp Phe Lys Thr Leu Arg Gln Gln Cys Leu
      35                  40                  45

GGA CTC AGG GGT CCT ATT TAA GGA CCC TGA GTT CCC AGC ATG TCC ATC     792
Asp Ser Gly Val Leu Phe Lys Asp Pro Glu Phe Pro Ala Cys Pro Ser
  50                  55                  60                  65

AGC TTT GGG CTA CAA GGA TCT TGG ACC AGG CTC TCC GCA AAC TCA AGG     840
Ala Leu Gly Tyr Lys Asp Leu Gly Pro Gly Ser Pro Gln Thr Gln Gly
                  70                  75                  80

CAT CAT CTG GAA GCG GCC CAC GGA GTT GTG TCC CAG CCC TCA GTT TAT     888
Ile Ile Trp Lys Arg Pro Thr Glu Leu Cys Pro Ser Pro Gln Phe Ile
          85                  90                  95
```

FIG. IA

```
CGT TGG TGG AGC CAC GCG CAC AGA CAT TTG TCA GGG TGG TCT AGG TGA    936
Val Gly Gly Ala Thr Arg Thr Asp Ile Cys Gln Gly Gly Leu Gly Asp
    100                 105                 110

CTG CTG GCT TCT GGC TGC CAT TGC CTC CCT GAC CCT GAA TGA AGA GCT    984
Cys Trp Leu Leu Ala Ala Ile Ala Ser Leu Thr Leu Asn Glu Glu Leu
    115                 120                 125

GCT TTA CCG GGT GGT CCC CAG GGA CCA GGA CTT CCA GGA GAA CTA TGC   1032
Leu Tyr Arg Val Val Pro Arg Asp Gln Asp Phe Gln Glu Asn Tyr Ala
    130                 135             140                 145

GGG AAT CTT TCA CTT TCA GTT CTG GCA GTA CGG AGA GTG GGT GGA GGT   1080
Gly Ile Phe His Phe Gln Phe Trp Gln Tyr Gly Glu Trp Val Glu Val
                    150                 155                 160

GGT CAT TGA CGA CAG GCT GCC CAC CAA GAA TGG ACA GCT GCT CTT CCT   1128
Val Ile Asp Asp Arg Leu Pro Thr Lys Asn Gly Gln Leu Leu Phe Leu
            165                 170                 175

ACA CTC GGA ACA AGG CAA TGA ATT CTG GAG TGC CCT GCT GGA GAA AGC   1176
His Ser Glu Gln Gly Asn Glu Phe Trp Ser Ala Leu Leu Glu Lys Ala
        180                 185                 190

CTA TGC CAA GCT TAA TGG TTG TTA TGA GGC TCT CGC TGG AGG TTC CAC   1224
Tyr Ala Lys Leu Asn Gly Cys Tyr Glu Ala Leu Ala Gly Gly Ser Thr
        195                 200                 205

AGT GGA GGG GTT TGA GGA TTT CAC AGG TGG CAT CTC TGA GTT TTA TGA   1272
Val Glu Gly Phe Glu Asp Phe Thr Gly Gly Ile Ser Glu Phe Tyr Asp
    210                 215                 220             225

CCT GAA GAA ACC ACC AGC CAA TCT ATA TCA GAT CAT CCG GAA GGC CCT   1320
Leu Lys Lys Pro Pro Ala Asn Leu Tyr Gln Ile Ile Arg Lys Ala Leu
            230                 235                 240

CTG TGC GGG GTC TCT GCT GGG CTG CTC CAT TGA TGT CTC CAG TGC AGC   1368
Cys Ala Gly Ser Leu Leu Gly Cys Ser Ile Asp Val Ser Ser Ala Ala
            245                 250                 255

CGA AGC CGA AGC CAT CAC CAG CCA GAA GCT GGT TAA GAG TCA TGC GTA   1416
Glu Ala Glu Ala Ile Thr Ser Gln Lys Leu Val Lys Ser His Ala Tyr
    260                 265                 270
```

FIG. 1B

| | |
|---|---|
| CTC TGT CAC TGG AGT CGA AGA GGT GAA TTT CCA GGG CCA TCC AGA GAA<br>Ser Val Thr Gly Val Glu Glu Val Asn Phe Gln Gly His Pro Glu Lys<br>275              280              285 | 1464 |
| GCT GAT CAG ACT CAG GAA TCC ATG GGG TGA AGT GGA GTG GTC GGG AGC<br>Leu Ile Arg Leu Arg Asn Pro Trp Gly Glu Val Glu Trp Ser Gly Ala<br>290              295              300              305 | 1512 |
| CTG GAG CGA TGA TGC ACC AGA GTG AAT CA CAT AGA CCC CCG GCG AAA<br>Trp Ser Asp Asp Ala Pro Glu Trp Asn His Ile Asp Pro Arg Arg Lys<br>310              315              320 | 1560 |
| GGA AGA ACT GGA CAA GAA AGT TGA GGA TGG AGA ATT CTG GAT GTC ACT<br>Glu Glu Leu Asp Lys Lys Val Glu Asp Gly Glu Phe Trp Met Ser Leu<br>325              330              335 | 1608 |
| TTC AGA TTT CGT GAG GCA GTT CTC TCG GTT GGA GAT CTG CAA CCT GTC<br>Ser Asp Phe Val Arg Gln Phe Ser Arg Leu Glu Ile Cys Asn Leu Ser<br>340              345              350 | 1656 |
| CCC GGA CTC TCT GAG TAG CGA GGA GGT GCA CAA ATG GAA CCT GGT CCT<br>Pro Asp Ser Leu Ser Ser Glu Glu Val His Lys Trp Asn Leu Val Leu<br>355              360              365 | 1704 |
| GTT CAA CGG CCA CTG GAC CCG GGG CTC CAC AGC TGG GGG CTG CCA GAA<br>Phe Asn Gly His Trp Thr Arg Gly Ser Thr Ala Gly Gly Cys Gln Asn<br>370              375              380              385 | 1752 |
| CTA CCC AGC CAC GTA CTG GAC CAA TCC CCA GTT CAA AAT CCG TTT GGA<br>Tyr Pro Ala Thr Tyr Trp Thr Asn Pro Gln Phe Lys Ile Arg Leu Asp<br>390              395              400 | 1800 |
| TGA AGT GGA TGA GGA CCA GGA GGA GAG CAT CGG TGA ACC TGC TGT AC<br>Glu Val Asp Glu Asp Gln Glu Glu Ser Ile Gly Glu Pro Cys Cys Thr<br>405              410              415 | 1848 |
| AGT GCT GCT GGG CCT GAT GCA GAA AAA TCG CAG GTG GCG GAA GCG GAT<br>Val Leu Leu Gly Leu Met Gln Lys Asn Arg Arg Trp Arg Lys Arg Ile<br>420              425              430 | 1896 |
| AGG ACA AGG CAT GCT TAG CAT CGG CTA TGC CGT CTA CCA GGT TCC AAA<br>Gly Gln Gly Met Leu Ser Ile Gly Tyr Ala Val Tyr Gln Val Pro Lys<br>435              440              445 | 1944 |

FIG. IC

| | |
|---|---|
| GGA GCT GGA GAG TCA CAC GGA CGC ACA CTT GGG CCG GGA TTT CTT CCT<br>  Glu Leu Glu Ser His Thr Asp Ala His Leu Gly Arg Asp Phe Phe Leu<br>  450                455            460            465 | 1992 |
| GGC CTA CCA GCC CTC AGC CCG CAC CAG CAC CTA CGT CAA CCT GCG GGA<br>  Ala Tyr Gln Pro Ser Ala Arg Thr Ser Thr Tyr Val Asn Leu Arg Glu<br>              470            475            480 | 2040 |
| GGT CTC TGG CCG GGC CCG GCT GCC CCC TGG GGA GTA CCT GGT GGT GCC<br>  Val Ser Gly Arg Ala Arg Leu Pro Pro Gly Glu Tyr Leu Val Val Pro<br>         485             490            495 | 2088 |
| ATC CAC ATT TGA ACC CTT CAA AGA CGG CGA GTT CTG CTT GAG AGT GTT<br>  Ser Thr Phe Glu Pro Phe Lys Asp Gly Glu Phe Cys Leu Arg Val Phe<br>         500             505            510 | 2136 |
| CTC AGA GAA GAA GGC CCA GGC CCT AGA AAT TGG GGA TGT GGT AGC TGG<br>  Ser Glu Lys Lys Ala Gln Ala Leu Glu Ile Gly Asp Val Val Ala Gly<br>         515             520            525 | 2184 |
| AAA CCC ATA TGA GCC ACA TCC CAG TGA GGT GGA TCA GGA AGA TGA CCA<br>  Asn Pro Tyr Glu Pro His Pro Ser Glu Val Asp Gln Glu Asp Asp Gln<br>  530                535            540            545 | 2232 |
| GTT CAG GAG GCT GTT TGA GAA GTT GGC AGG GAA GGA TTC TGA GAT TAC<br>  Phe Arg Arg Leu Phe Glu Lys Leu Ala Gly Lys Asp Ser Glu Ile Thr<br>              550            555            560 | 2280 |
| TGC CAA TGC ACT CAA GAT ACT TTT GAA TGA GGC GTT TTC CAA GAG AAC<br>  Ala Asn Ala Leu Lys Ile Leu Leu Asn Glu Ala Phe Ser Lys Arg Thr<br>         565             570            575 | 2328 |
| AGA CAT AAA ATT CGA TGG ATT CAA CAT CAA CAC TTG CAG GGA AAT GAT<br>  Asp Ile Lys Phe Asp Gly Phe Asn Ile Asn Thr Cys Arg Glu Met Ile<br>         580             585            590 | 2376 |
| CAG TCT GTT GGA TAG CAA TGG AAC GGG CAC TTT GGG GGC GGT GGA ATT<br>  Ser Leu Leu Asp Ser Asn Gly Thr Gly Thr Leu Gly Ala Val Glu Phe<br>         595             600            605 | 2424 |
| CAA GAC GCT CTG GCT GAA GAT TCA GAA GTA TCT GGA GAT CTA TTG GGA<br>  Lys Thr Leu Trp Leu Lys Ile Gln Lys Tyr Leu Glu Ile Tyr Trp Glu<br>  610                615            620            625 | 2472 |

FIG. ID

```
AAC TGA TTA TAA CCA CTC GGG CAC CAT CGA TGC CCA CGA GAT GAG GAC   2520
 Thr Asp Tyr Asn His Ser Gly Thr Ile Asp Ala His Glu Met Arg Thr
             630                 635                 640

AGC CCT CAG GAA GGC AGG TTT CAC CCT CAA CAG CCA GGT GCA GCA GAC   2568
 Ala Leu Arg Lys Ala Gly Phe Thr Leu Asn Ser Gln Val Gln Gln Thr
             645                 650                 655

CAT TGC CCT GCG GTA TGC GTG CAG CAA GCT CGG CAT CAA CTT TGA CAG   2616
 Ile Ala Leu Arg Tyr Ala Cys Ser Lys Leu Gly Ile Asn Phe Asp Ser
             660                 665                 670

CTT CGT GGC TTG TAT GAT CCG CCT GGA GAC CCT CTT CAA ACT ATT CAG   2664
 Phe Val Ala Cys Met Ile Arg Leu Glu Thr Leu Phe Lys Leu Phe Ser
          675                 680                 685

CCT TCT GGA CGA AGA CAA GGA TGG CAT GGT TCA GCT CTC TCT GGC CGA   2712
 Leu Leu Asp Glu Asp Lys Asp Gly Met Val Gln Leu Ser Leu Ala Glu
     690                 695                 700                 705

GTG GCT GTG CTG CGT GTT GGT C TGACCCG GGGTTTCGGA CATCAGTGAC ACTCCC  2767
 Trp Leu Cys Cys Val Leu Val
                 710
```

```
TGCCCCACTG CTTGCTTCTT GTCACCCCTT CTCTACAATT TTGTGAACAT TTATGCTCCA   2827
GTGGCATTCA CTGGTTGTTC ATACCTTTCT TGCCCTGGGT CTATTTCAGC AGCACTGAGC   2887
TATGAGCTAT GTAAGCCGAC CCGGTGGGCC CAGTGGAGGG AAAGCAATCA ATTAAAGTTG   2947
TGAGCCAGAA AAAAAAAAAA AAA                                          2970
```

FIG. IE

```
ATG TTC CTG GTT AAC TCG TTC TTG AAG GGC GGC GGC GGC GGC GGC GGG   48
Met Phe Leu Val Asn Ser Phe Leu Lys Gly Gly Gly Gly Gly Gly Gly
 1               5                  10                  15

GGA GGC GGG GGC CTG GGT GGG GGC CTG GGA AAT GTG CTT GGA GGC CTG   96
Gly Gly Gly Gly Leu Gly Gly Gly Leu Gly Asn Val Leu Gly Gly Leu
                20                  25                  30

ATC AGC GGG GCC GGG GGC GGC GGC GGC GGC GGC GGC GGC GGC GGC GGT  144
Ile Ser Gly Ala Gly Gly Gly Gly Gly Gly Gly Gly Gly Gly Gly Gly
            35                  40                  45

GGT GGA GGC GGC GGT GGC GGT GGA ACG GCC ATG CGC ATC CTA GGC GGA  192
Gly Gly Gly Gly Gly Gly Gly Gly Thr Ala Met Arg Ile Leu Gly Gly
        50                  55                  60

GTC ATC AGC GCC ATC AGC GAG GCG GCT GCG CAG TAC AAC CCG GAG CCC  240
Val Ile Ser Ala Ile Ser Glu Ala Ala Ala Gln Tyr Asn Pro Glu Pro
65                  70                  75                  80

CCG CCC CCA CGC ACA CAT TAC TCC AAC ATT GAG GCC AAC GAG AGT GAG  288
Pro Pro Pro Arg Thr His Tyr Ser Asn Ile Glu Ala Asn Glu Ser Glu
                85                  90                  95

GAG GTC CGG CAG TTC CGG AGA CTC TTT GCC CAG CTG GCT GGA GAT GAC  336
Glu Val Arg Gln Phe Arg Arg Leu Phe Ala Gln Leu Ala Gly Asp Asp
                100                 105                 110

ATG GAG GTC AGC GCC ACA GAA CTC ATG AAC ATT CTC AAT AAG GTT GTG  384
Met Glu Val Ser Ala Thr Glu Leu Met Asn Ile Leu Asn Lys Val Val
            115                 120                 125

ACA CGA CAC CCT GAT CTG AAG ACT GAT GGT TTT GGC ATT GAC ACA TGT  432
Thr Arg His Pro Asp Leu Lys Thr Asp Gly Phe Gly Ile Asp Thr Cys
        130                 135                 140

CGC AGC ATG GTG GCC GTG ATG GAT AGC GAC ACC ACA GGC AAG CTG GGC  480
Arg Ser Met Val Ala Val Met Asp Ser Asp Thr Thr Gly Lys Leu Gly
145                 150                 155                 160

TTT GAG GAA TTC AAG TAC TTG TGG AAC AAC ATC AAA AGG TGG CAG GCC  528
Phe Glu Glu Phe Lys Tyr Leu Trp Asn Asn Ile Lys Arg Trp Gln Ala
                165                 170                 175
```

FIG. 2A

```
ATA TAC AAA CAG TTC GAC ACT GAC CGA TCA GGG ACC ATT TGC AGT AGT  576
Ile Tyr Lys Gln Phe Asp Thr Asp Arg Ser Gly Thr Ile Cys Ser Ser
            180                 185                 190

GAA CTC CCA GGT GCC TTT GAG GCA GCA GGG TTC CAC CTG AAT GAG CAT  624
Glu Leu Pro Gly Ala Phe Glu Ala Ala Gly Phe His Leu Asn Glu His
            195                 200                 205

CTC TAT AAC ATG ATC ATC CGA CGC TAC TCA GAT GAA AGT GGG AAC ATG  672
Leu Tyr Asn Met Ile Ile Arg Arg Tyr Ser Asp Glu Ser Gly Asn Met
    210                 215                 220

GAT TTT GAC AAC TTC ATC AGC TGC TTG GTC AGG CTG GAC GCC ATG TTC  720
Asp Phe Asp Asn Phe Ile Ser Cys Leu Val Arg Leu Asp Ala Met Phe
225                 230                 235                 240

CGT GCC TTC AAA TCT CTT GAC AAA GAT GGC ACT GGA CAA ATC CAG GTG  768
Arg Ala Phe Lys Ser Leu Asp Lys Asp Gly Thr Gly Gln Ile Gln Val
                245                 250                 255

AAC ATC CAG GAG TGG CTG CAG CTG ACT ATG TAT TCC TGA              807
Asn Ile Gln Glu Trp Leu Gln Leu Thr Met Tyr Ser •
            260                 265
```

FIG. 2B

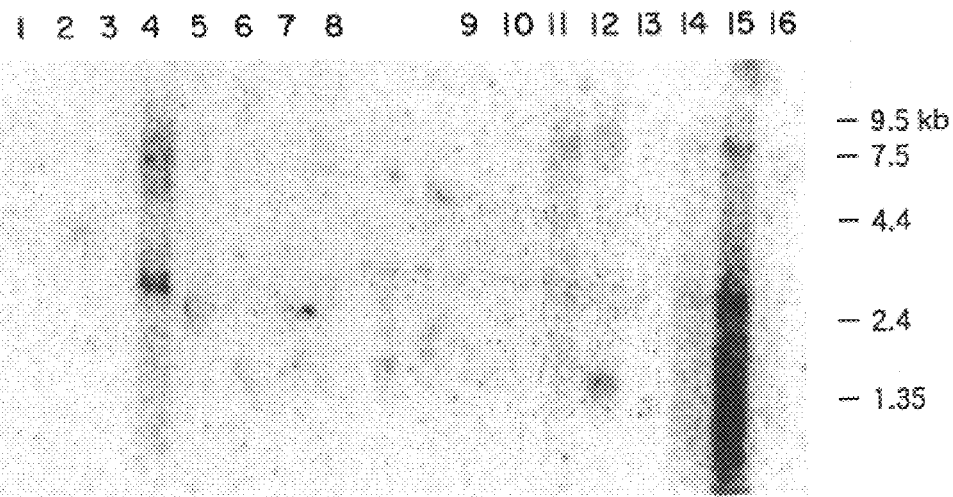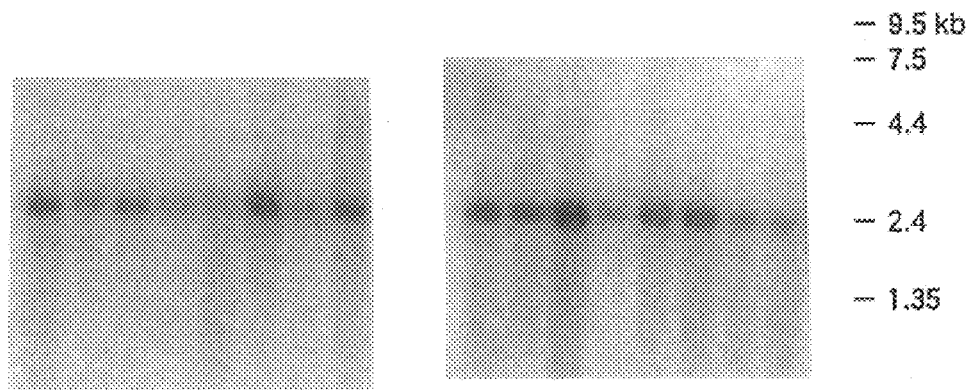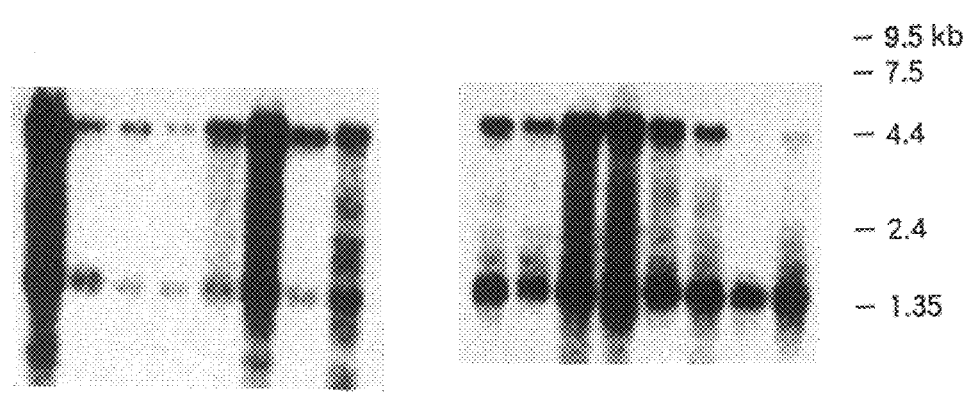

PROTEINS, THEIR PRODUCTION AND USE

This application is a divisional application of Ser. No. 08/835,099 filed Apr. 4, 1997, now U.S. Pat. No. 5,874,277. This application claims priority under 119 to Japanese document 087649/1996 filed May 4, 1996.

FIELD OF THE INVENTION

The present invention relates to a novel protein showing an activity of calpain which is a calcium-dependent neutral protease.

BACKGROUND OF THE INVENTION

There are some proteins which require a qualitative modification for their activation. The modification is usually carried out post-translationally (e.g. phosphorylation, processing, lipid modification) and through interactions with other proteins (e.g. binding subunits, endogenous inhibitors). Therefore, if the above regulation would be disturbed, a variety of pathological processes might be induced and cause cell death or tissue destruction. Proteases present as a modulator of intracellular signalling and capable of regulating other intracellular proteins are attractive pharmaceutical target to investigate (Trends in Biological Science, 14, 268–271 (1989)).

Calpain is an intracellular cysteine protease, the activity of which is regulated by calcium ions. It has therefore been believed that calpain functions as a regulatory molecule in cellular functions. Two calpains, μ-calpain and m-calpain, which require low and high micromolar $Ca^{2+}$ concentration for activation, respectively, were discovered in poultry and many mammalian animals in an early stage of research. Recently, several calpains have been reported in nematodes and Drosophilas (e.g. sol and CalpA from Drosophilas and Ce-CL2 and Ce-CL3 from nematodes). Furthermore, two tissue-specific calpains also have been discovered in higher vertebrates. They are p94 (nCL-1), which is specifically expressed in the skeletal muscles of human, rat, and chicken, and nCL-2 and nCL-2', which are reported to be most highly expressed in the stomach of rats. It is known that some of modulating proteins (e.g. protein kinase C, MAP kinase) comprises a large number of isoforms to control diverse cellular functions. Therefore, it is believed that unknown calpains isoforms exist. At the present time, in humans, only three calpains are known, μ-calpain and m-calpain, which are ubiquitous in vertebrate tissues, and p94 (nCL-1).

Isolation of novel calpains can provide a new pharmaceutical compound and composition for treatment of diseases where normal levels of calpain are lacking, thus causing a loss of control of cell growth, i.e., diseases such as cancer. Discovery and isolation of new calpains also will contribute to a still further detailed exploration into the implication of calpain in the $Ca^{2+}$-activated signal transduction system and, should it be found to be tissue-specific, into the relationship of calpain with various tissue-specific diseases. It would also enable us to develop new drugs which would either activate or inhibit an activity of the calpain and thus be useful for the prevention and therapy of various diseases. Thus, in the technological area to which the present invention pertains, there has been a standing need for isolating novel human calpain isoforms and for developing a method for high production of such calpains.

The inventors of the present invention did much research for solving the above problems and succeeded in cloning a cDNA having a novel nucleotide sequence from a human leukocyte-derived cDNA library. They found that the protein encoded by this cDNA is a calpain. The present inventors made further investigations based on these findings, and accomplished the present invention.

SUMMARY OF THE INVENTION

The present invention provides:

(1) A protein comprising an amino acid sequence represented by SEQ ID NO. 1 or a substantial equivalent thereto, or a salt thereof, (2) The protein according to (1), which comprises an amino acid sequence represented by SEQ ID NO. 2, (3) The protein according to (1), which is a human calpain, (4) A partial peptide of the protein according to (1), which shows the activity of the protein according to (1), (5) An isolated DNA which contains a DNA comprising a nucleotide sequence coding for the protein according to (1), (6) The DNA according to (5), which comprises a nucleotide sequence represented by SEQ ID NO. 5 or SEQ ID NO. 6, (7) A recombinant vector comprising the DNA according to (5), (8) A transformant carrying the recombinant vector according to (7), (9) A process for producing a protein or a salt thereof according to (1), which comprises culturing a transformant according to (8) under conditions suitable to express the protein,

(10) A pharmaceutical composition which comprises the DNA according to (5),

(11) The pharmaceutical composition according to (10), which is a therapeutic or prophylactic composition for cancer, cerebral apoplexy, cerebral infarction, subarachnoid hemorrhange, Alzheimer's disease, myodystrophy, cataract, ischemic heart disease, atherosclerosis, arthritis or collagen disease,

(12) An antibody against the protein according to (1) or the partial peptide according to (4),

(13) A method for screening for a compound which activates or inhibits a proteolytic activity of the protein according to (1) or the partial peptide according to (4), which comprises measuring and comparing a proteolytic activity of the protein according to (1) or the partial peptide according to (4), in case of (i) a substrate is contacted with the protein according to (1) or the partial peptide according to (4) and (ii) a substrate and a test compound are contacted with the protein according to (1) or the partial peptide according to (4),

(14) A kit for screening for a compound which activates or inhibits a proteolytic activity of the protein according to (1) or the partial peptide according to (4), which comprises the protein according to (1) or the partial peptide according to (4),

(15) A compound which activates or inhibits a proteolytic activity of the protein according to (1) or the partial peptide according to (4), which is identified by the screening method according to (13) or the kit according to (14), and

(16) A method for treating or preventing cancer, cerebral apoplexy, cerebral infarction, subarachnoid hemorrhange, Alzheimer's disease, myodystrophy, cataract, ischemic heart disease, atherosclerosis, arthritis or collagen disease in a mammal, which comprises administering an effective amount of the DNA according to (5) to the mammal.

Moreover, the present invention provides:

(17) An isolated DNA which hybridizes under highstringent condition to a DNA comprising a nucleotide sequence represented by SEQ ID NO. 5 or SEQ ID NO. 6,

(18) A recombinant vector comprising the DNA according to (17),

(19) A transformant carrying the recombinant vector according to (18),

(20) A process for producing a protein or a salt thereof comprising culturing a transformant according to (19) under conditions suitable to express the protein,

(21) A protein produced by the process according to (20),

(22) A pharmaceutical composition which comprises the compound which activates a proteolytic activity of the protein according to (1) or the partial peptide according to (4), which is identified by the screening method according to (13) or the kit according to (14),

(23) The pharmaceutical composition according to (22) which is a therapeutic or prophylactic composition for cancer,

(24) A pharmaceutical composition which comprises the compound which inhibits a proteolytic activity of the protein according to (1) or the partial peptide according to (4), which is identified by the screening method according to (13) or the kit according to (14),

(25) The pharmaceutical composition according to (24) which is a therapeutic or prophylactic composition for cerebral apoplexy, cerebral infarction, subarachnoid hemorrhange, Alzheimer's disease, myodystrophy, cataract, ischemic heart disease, atherosclerosis, arthritis or collagen disease,

(26) A method of quantitative determination of the protein according to (1) or the partial peptide according to (4) in test liquid sample, which comprises
(a) competitively reacting the test liquid sample and a labeled protein according to (1) or partial peptide according to (4) with the antibody according to (12), and
(b) measuring the ratio of the labeled protein according to (1) or partial peptide according to (4) binding with the antibody, and

(27) A method of quantitative determination of the protein according to (1) or the partial peptide according to (4) in test liquid sample, which comprises
(a) reacting the test liquid sample with the antibody according to (12) immobilized on an insoluble carrier and a labeled antibody according to (12) simultaneously or continuously, and
(b) measuring the activity of the labeling agent on the insoluble carrier.

BRIEF DESCRIPTION OF THE DRAWINGS

FIG. 1 shows the nucleotide sequence (SEQ ID NO:6) of the DNA encoding the human captain of the present invention and the amino acid sequence (SEQ ID NO:2) of the human calpain encoded by the DNA.

FIG. 2 shows the nucleotide sequence (SEQ ID NO:10) of the DNA encoding human calpain small subunit and the amino acid sequence (SEQ ID NO:9) of the protein encoded by the DNA.

FIGS. 3A, 3B, 3C and 3D show the electrophoretogram of Northern blot analysis for mRNAs prepared from various human tissues, where (1) represents heart, (2) brain, (3) placenta, (4) lung, (5) liver, (6) skeletal muscle, (7) kidney, (8) pancreas, (9) spleen, (10) thymus, (11) prostate, (12) testis, (13) ovary, (14) small intestine, (15) large intestine, and (16) peripheral white blood cell. FIGS. 3A, 3B, 3C and 3D show the amounts of expression of mRNA encoding the human calpain of the present invention, large subunit of $\mu$-calpain, small subunit of calpain and $\beta$-actin, respectively. The figure at right (kb) represents the size of RNA molecular weight marker.

DESCRIPTION OF THE PREFERRED EMBODIMENTS

The protein comprising an amino acid sequence represented by SEQ ID NO. 1 or its substantial equivalent thereto of the present invention (hereinafter referred to as the protein of the present invention) may be (1) a protein derived from cells of human and other warm-blooded animals (e.g. guinea pig, rat, mouse, chicken, rabbit, swine, sheep, bovine, monkey, etc.) such as liver cell, splenocytes, nerve cell, glia cell, B cell, bone marrow cell, mesangial cell, Langerhans' cell, epidermic cell, epithelial cell, endothelial cell, fibroblast, fibrocyte, myocyte, fat cell, immune cell (e.g. macrophage, T cell, B cell, natural killer cell, mast cell, neutorphil, basophil, eosinophil, monocyte), megakaryocyte, synovial cell, chondrocyte, bone cell, osteoblast, osteoclast, mammary gland cell, hepatocyte, interstitial cell, etc., the corresponding precursor cells, stem cells, cancer cells, etc., or any tissues where such cells are present, such as brain or any of its regions (e.g. olfactory bulb, amygdaloid nucleus, basal ganglia, hippocampus, thalamus, hypothalamus, cerebral cortex, medulla oblongata, cerebellum, etc.), spinal cord, hypophysis, stomach, pancreas, kidney, liver, gonad, thyroid, gallbladder, bone marrow, adrenal gland, skin, muscle, lung, gastrointestinal tract (e.g. large intestine and small intestine), blood vessel, heart, thymus, spleen, submandibular gland, peripheral blood, prostate, testis, ovary, placenta, uterus, bone, joint, skeletal muscle, etc., (2) a protein derived from cultured human cell lines (e.g. MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.), or (3) synthetic protein.

Examples of the substantial equivalent amino acid sequence to the amino acid sequence represented by SEQ ID NO. 1 are an amino acid sequence of not less than about 85%, preferably not less than about 90%, more preferably not less than about 95% identity to the amino acid sequence represented by SEQ ID NO. 1 and so on. More preferable examples are (1) an amino acid sequence of not less than about 85%, preferably not less than about 90%, more preferably not less than about 95% identity to the amino acid sequence represented by SEQ ID NO. 1, which comprises an amino acid sequence represented by SEQ ID NO. 3 or/and SEQ ID NO. 4, (2) an amino acid sequence of not less than about 85%, preferably not less than about 90%, more preferably not less than about 95% identity to the amino acid sequence represented by SEQ ID NO. 2, which comprises an amino acid sequence represented by SEQ ID NO. 3 or/and SEQ ID NO. 4, and so on.

Examples of the protein comprising a substantial equivalent to the amino acid sequence represented by SEQ ID NO. 1 are a protein which comprises a substantial equivalent amino acid sequence to the amino acid sequence represented by SEQ ID NO. 1 and has a substantial equivalent activity to the protein comprising the amino acid sequence represented by SEQ ID NO. 1, and so on.

Examples of the substantial equivalent activity are a proteolytic activity (e.g. activity of proteases such as proteinases, peptidases, etc.), a binding activity to $Ca^{2+}$ and other activities of the calpain of the present invention. The term "substantial equivalent" means that the nature of these activities are equivalent. Therefore, it is preferred that the strength of these activities such as a proteolytic activity and a binding activity to $Ca^{2+}$ is equivalent (e.g. about 0.1 to about 100 times, preferably about 0.5 to about 10 times, more preferably about 0.5 to about 2 times), and it is allowable that even differences among grades such as the strength of these activities and molecular weight of the protein are present.

Activities such as a proteolytic activity and a binding activity to $Ca^{2+}$ may be measured by per se known methods. For example, they may be measured by the method for screening as mentioned below.

The proteins of the present invention include muteins such as proteins comprising (1) an amino acid sequence wherein 1 or more amino acid residues (for example 1 to 30, preferably 1 to 10, more preferably a few amino acid residues) are deleted from the amino acid sequence represented by SEQ ID NO. 1 or SEQ ID NO. 2, (2) an amino acid sequence wherein 1 or more amino acid residues (for example 1 to 30, preferable 1 to 10, more preferable a few amino acid residues) are added to the amino acid sequence represented by SEQ ID NO. 1 or SEQ ID NO. 2, (3) an amino acid sequence wherein 1 or more amino acid residues (for example 1 to 30, preferably 1 to 10, more preferably a few amino acid residues) in the amino acid sequence represented by SEQ ID NO. 1 or SEQ ID NO. 2 are substituted with one or more other amino acid residues, or (4) combinations thereof.

When the amino acid sequence of the proteins are deleted or substituted as mentioned above, examples of the positions of deletion or substitution are, for example, other than (1) 98th to 105th amino acid sequence of the amino acid sequence represented by SEQ ID NO. 1 (an amino acid sequence represented by SEQ ID NO. 3), (2) 262nd to 286th amino acid sequence of the amino acid sequence represented by SEQ ID NO. 1 (an amino acid sequence represented by SEQ ID NO. 4) and so on.

When the amino acid sequence of the proteins are added as mentioned above, examples of amino acid sequences are an amino acid sequence represented by SEQ ID NO. 2 wherein 9 amino acids residues are added to the N-terminus of the amino acid sequence represented by SEQ ID NO. 1.

Throughout this specification, proteins are represented in accordance with the conventions for description of peptides, that is the N-terminus (amino terminus) at left and the C-terminus (carboxyl terminus) at right. The protein of the present invention including the protein containing the amino acid sequence of SEQ ID NO:1 is usually in the carboxyl (—COOH) or carboxylate (—COO$^-$) form at the C-terminus but may be in the amide (—CONH$_2$) or ester (—COOR) form.

The ester residue R includes a $C_{1-6}$ alkyl group (e.g. methyl, ethyl, n-propyl, isopropyl, n-butyl, etc., a $C_{3-8}$ cycloalkyl group (e.g. cyclopentyl, cyclohexyl, etc.), a $C_{6-12}$ aryl group (e.g. phenyl, α-naphthyl, etc.), a $C_{7-14}$ aralkyl group such as a phenyl-$C_{1-2}$ alkyl group (e.g. benzyl, phenethyl, etc.) and α-naphthyl-$C_{1-2}$ alkyl, (e.g. α-naphthylmethyl, etc.), as well as pivaloyloxymethyl which is universally used for the production of esters for oral administration.

When the protein of the present invention has a carboxyl (or carboxylate) function in any position other than the C-terminus, the corresponding carboxamide or ester form is also included in the scope of the invention. The ester mentioned just above may be any of the esters mentioned for the C-terminal carboxyl function.

Furthermore, the protein of the present invention includes (1) the protein in which the N-terminal Met has been protected with a protective group (e.g. $C_{1-6}$ acyl such as formyl or acetyl, etc.), (2) the protein in which the N-terminal side of Glu has been cleaved in vivo to form pyroglutamine, (3) the protein in which the side chain of any relevant constituent amino acid (e.g. OH, COOH, NH$_2$, SH) has been protected by any protective group (e.g. a formyl group, an acetyl group, etc.), and (4) the complex protein such as glycoproteins available upon attachment of sugar chains.

Preferable Examples of the proteins of the present invention are human calpain such as a human leukocyte-derived protein comprising an amino acid sequence represented by SEQ ID NO. 1 or SEQ ID NO. 2 (FIG. 1).

Examples of the partial peptide of the present invention are any partial peptides of the protein of the present invention as mentioned above which have a proteolytic activity. For example, the partial peptides include peptides comprising at least not less than about 20, preferably not less than about 50, more preferably not less than about 70, for still better result, not less than about 100, best result, not less than 200 amino acid residues of the amino acid sequence of the proteins of the present invention.

Preferable examples of the partial peptide of the present invention are a peptide which comprises an amino acid sequence represented by SEQ ID NO. 3 or/and SEQ ID NO. 4, or its substantial equivalent thereto and has a substantial equivalent activity to the protein comprising the amino acid sequence represented by SEQ ID NO. 1.

Examples of the substantial equivalent amino acid sequence to the amino acid sequence represented by SEQ ID NO. 3 or/and SEQ ID NO. 4 are an amino acid sequence of not less than about 85%, preferably not less than about 90%, more preferably not less than about 95% identity to the amino acid sequence represented by SEQ ID NO. 3 or/and SEQ ID NO. 4.

The amino acid sequence represented by SEQ ID NO. 3 shows an amino acid sequence from $^{98}$Cys to $^{105}$Cys of the amino acid sequence represented by SEQ ID NO. 1, and the amino acid sequence represented by SEQ ID NO. 4 shows an amino acid sequence from $^{262}$His to $^{286}$Asn of the amino acid sequence represented by SEQ ID NO. 1. The both amino acid sequences show amino acid sequences of catalytic domain of the protein of the present invention.

The term "substantial equivalent activity" has the same meaning as defined above. The "substantial equivalent activity" can be measured by the same method as mentioned above.

In the partial peptides of the present invention, 1 or more amino acid residues (preferably 1 to 10, more preferably a few amino acid residues) of its amino acid sequence may be deleted, or 1 or more amino acid residues (preferably 1 to 10, more preferably a few amino acid residues) may be added to its amino acid sequence, or 1 or more amino acid residues (preferably 1 to 10, more preferably a few amino acid residues) in its amino acid sequence may be substituted with one or more other amino acid residues.

The peptide of the present invention is usually in the carboxyl (—COOH) or carboxylate (—COO$^-$ form at the C-terminus, but may instead be in the amide (—CONH$_2$) or ester (—COOR) form as same as the protein of the present invention as mentioned above.

Furthermore, the partial peptide of the present invention includes (1) the peptide in which the N-terminal Met has been protected with a protective group, (2) the peptide in which the N-terminal side of Glu has been cleaved in vivo to form pyroglutamine, (3) the peptide in which the side chain or any relevant constituent amino acid has been protected by any protective group, and (4) the complex peptide such as glycoproteins available upon attachment of sugar chains as same as the protein of the present invention as mentioned above.

The salt of the protein or the partial peptide of the present invention includes salts with physiologically acceptable bases, e.g. alkali metals or acids such as organic or inorganic acids, and is preferably a physiologically acceptable acid addition salt. Examples of such salts are salts thereof with inorganic acids (e.g. hydrochloric acid, phosphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.)

The protein or a salt thereof of the present invention can be produced from the tissues or cells of human or other warm-blooded animals by the per se known purification technology or, as described hereinafter, by culturing a transformant carrying a DNA encoding the protein. It can also be produced in accordance with the procedures for peptide synthesis which are described hereinafter.

When the protein of the present invention is produced from the tissues or cells of human or other warm-blooded animals, the tissues or cells of human or other warm-blood animals is homogenized and the protein of the present invention is extracted by acids, etc. The protein can be purified and isolated from the extracted solution by a combination of chromatography such as reverse phase chromatography, ion exchange chromatography and so on.

For the synthesis of the protein of the present invention, a partial peptide thereof or their salts, or their amides form, any of the commercial resins available for protein synthesis can be employed. Among such resins are chloromethyl resin, hydroxymethyl resin, benzhydrylamino resin, aminomethyl resin, 4-benzyloxybenzyl alcohol resin, 4-methylbenzhydrylamino resin, PAM resin, 4-hydroxymethyl-methylphenylacetamidomethyl resin, polyacrylamide resin, 4-(2',4'-dimethoxyphenyl-hydroxymethyl)phenoxy resin, and 4-(2',4'-dimethoxyphenyl-Fmoc-aminoethyl)phenoxy resin. Using such a resin, amino acids which may be protected at side-chain functional groups in a suitable manner beforehand can be serially condensed with the α-amino group in the order corresponding to the amino acid sequence of the objective protein by various condensation techniques which are per se known. After completion of the final condensation reaction, the protein is cut out from the resin and the protective groups are removed. Then, in highly diluted solution, the intramolecular disulfide-forming reaction is carried out to provide the objective proteins or amides thereof.

Referring to the above condensation of protected amino acids, various activators known to be useful for protein synthesis can be utilized, and carbodiimide reagents are especially preferred. The carbodiimide reagents include are DCC, N,N'-diisopropylcarbodiimide, and N-ethyl-N'-(3-dimethylaminoprolyl)carbodiimide and so on. For activation by these reagents, the protected amino acid and a recemization inhibitor (e.g. HOBt, HOOBt, etc.) can be directly added to the resin, or the protected amino acid can be activated beforehand in the form of symmetric acid anhydride, HOBt ester or HOOBt ester and, then, added to the resin.

The solvent used for the above-mentioned activation of protected amino acids or the conjugation thereof to the resin can be liberally selected from among the solvents known to be useful for protein condensation reactions. Example of the solvent are acid amides (e.g. N,N-dimethylformamide, N,N-dimethylacetamide, N-methylpyrrolidone, etc.), halogenated hydrocarbons (e.g. methylene chloride, chloroform, etc.), alcohols (e.g. trifluoroethanol, sulfoxides (e.g. dimethyl sulfoxide, etc.), ethers (e.g. pyridine, dioxane, tetrahydrofuran, etc.), nitriles (e.g. acetonitrile, propionitrile, etc.), esters (e.g. methyl acetate, ethyl acetate, etc.), and suitable mixtures of these solvents. The reaction temperature can be selected from the range known to be useful for protein-forming reactions, usually the range of about −20° C. to about 50° C. The activated amino acid derivative is generally used in a 1.5 to 4-fold excess. When the condensation is found insufficient by ninhydrin assay, the reaction can be repeated to make the sufficient condensation thorough. When sufficient condensation can not be achieved by repeated reaction, the unreacted amino acid can be acetylated by using acetic anhydride or acetylimidazole.

The protective groups for protecting the amino group of the starting compound include Z, Boc, tert-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc, and so on.

The carboxyl group can be protected in the form of, for example, an alkyl ester (e.g. straight-chain, branched, or cyclic alkyl esters such as methyl, ethyl, propyl, butyl, tert-butyl, cyclopentyl, cyclohexyl, cycloheptyl, cyclooctyl, 2-adamantyl, and so on), an aralkyl ester (e.g. benzyl, 4-nitrobenzyl, 4-methoxybenzyl, 4-chlorobenzyl, benzhydryl, and so on), phenacyl ester, benzyloxycarbonylhydrazide, tert-butoxycarbonylhydrazide or tritylhydrazide.

The hydroxyl group of serine can be protected in the form of an ester or an ether. The group suitable for esterification includes carboxylic acid-derived acyl groups such as a lower alkanoyl group (e.g. acetyl, etc.), an aroyl group (e.g. benzoyl, etc.), a benzyloxycarbonyl, an ethoxycarbonyl group and so on. The group suitable for etherification includes a benzyl group, a tetrahydropyranyl group, a t-butyl group and so on.

The protective group used for protecting the phenolic hydroxyl group of tyrosine includes Bzl, Cl$_2$-Bzl, 2-nitrobenzyl, Br-Z, tert-butyl and so on.

The protective group for the imidazole group of histidine includes Tos, 4-methoxy-2,3,6-trimethylbenzenesulfonyl, DNP, benzyloxymethyl, Bum, Boc, Trt, Fmoc and so on.

The starting compound with activated carboxy groups includes the corresponding acid anhydride, azide, and active ester (e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc.). The starting compound with activated amino groups includes the corresponding phosphoric acid amide.

The method for removal of such protective groups includes catalytic reduction in a hydrogen stream in the presence of a catalyst (e.g. Pd black or Pd-on-carbon), acid treatment with anhydrous hydrogen fluoride, methanesulfonic acid, trifluoromethanesulfonic acid, trifluoroacetic acid or a mixture thereof, treatment with a base such as diisopropylethylamine, triethylamine, piperidine, piperazine or the like, and reduction with sodium metal in liquid ammonia. The above deprotection by treatment with acid is generally conducted at a temperature of about −20° C. to 40° C. This acid treatment can be carried out advantageously in the presence of a cation acceptor such as anisole, phenol, thioanisole, m-cresol, p-cresol, dimethyl sulfide, 1,4-butanedithiol, 1,2-ethanedithiol, or the like. The 2,4-dinitrophenyl group used for protecting the imidazole group of histidine can be removed by treatment with thiophenol, and the formyl group used for protecting the indole group of tryptophan can be removed not only by said acid treatment in the presence of 1,2-ethanedithiol, 1,4-butanedithiol or the like as described hereinbefore, but also by alkali treatment with diluted sodium hydroxide solution, diluted liquid ammonia, or the like.

The method for protecting any functional group that should not take part in the contemplated reaction, the protective group to be used for such protection, the method for eliminating the protective group, and the method for activating the functional group to be involved in the contemplated reaction can all be liberally selected from among the known methods and groups.

An alternative method for providing the protein in amide form typically comprises protecting the α-carboxyl group of the C-terminal amino acid in the form of an amide, extending the peptide (protein) chain to a desired length towards the N-terminus, deprotecting the N-terminal α-amino acid of the resulting peptide chain selectively to provide an N-terminal-deprotected fragment, preparing a peptide (protein) fragment with its C-terminal carboxyl group selectively deprotected, and condensing the two fragments in a solvent such as the mixed solvent mentioned hereinbefore. The condensation reaction can be carried out in the same manner as described hereinbefore. After purification of the protected protein thus obtained by condensation, all the protective groups are eliminated by the procedures described hereinbefore to provide the contemplated protein in crude form. This crude protein is purified by suitable known purification techniques and lyophilized to provide the desired protein amide.

A method for providing the protein in an ester form comprises condensing the α-carboxyl group of the C-terminal amino acid with suitable alcohols to prepare the corresponding ester and subjecting this ester to the same procedure as described for purification of the protein amide to provide the objective protein ester.

The partial peptide of the protein of the present invention or a salt thereof can be produced by per se known procedures for peptide synthesis or by cleaving the protein with a suitable peptidase. The process for peptide synthesis may be a solid-phase synthesis and/or a liquid-phase synthesis. Namely, the objective peptide can be produced by condensing a partial peptide or amino acid capable of constituting the protein with the residual part thereof and, when the product has a protective group, the protective group is removed whereupon a desire peptide can be manufactured. The known technology for condensation and deprotection includes the procedures described in the following literature (1)–(5).

(1) M. Bodanszky and M. A. Ondetti, Peptide Synthesis, Interscience Publishers, New York, 1966

(2) Schroeder and Luebke, The Peptide, Academic Press, New York, 1965

(3) Nobuo Izumiya et al., Fundamentals and Experiments in Peptide Synthesis, Maruzen, 1975

(4) Haruaki Yajima and Shumpei Sakakibara, Biochemical Experiment Series 1, Protein Chemistry IV, 205, 1977

(5) Haruaki Yajima (ed.), Development of Drugs-Continued, 14, Peptide Synthesis, Hirokawa Shoten After the reaction, the partial peptide of the present invention can be purified and isolated by a combination of conventional purification techniques such as solvent extraction, distillation, column chromatography, liquid chromatography, and recrystallization. When the partial peptide isolated as above is a free compound, it can be converted to a suitable salt by known methods.

The DNA coding for the protein of the present invention may be any DNA comprising a nucleotide sequence encoding the protein of the present invention as mentioned above. It may also be any one of genomic DNA, genomic DNA library, cDNA derived from the tissues or cells as mentioned above, cDNA library derived from the tissues or cells as mentioned above, and synthetic DNA.

The vector for constructing a library may include bacteriophage, plasmid, cosmid, and phagemid. Furthermore, using a totalRNA fraction or an mRNA fraction prepared from the tissues or cells, a direct amplification can be carried out by the RT-PCR technique.

Examples of DNA coding for the protein of the present invention are (1) a DNA comprising a nucleotide sequence represented by SEQ ID NO. 5, or a DNA which comprises a nucleotide sequence hybridizing to the nucleotide sequence represented by SEQ ID NO. 5 under highstringent condition and codes for a protein having a substantial equivalent activity to the protein comprising the amino acid sequence represented by ID No. 1, (2) a DNA comprising a nucleotide sequence represented by SEQ ID NO. 6, or a DNA which comprises a nucleotide sequence hybridizing to the nucleotide sequence represented by SEQ ID NO. 6 under highstringent condition and codes for a protein having a substantial equivalent activity to the protein comprising the amino acid sequence represented by SEQ ID NO. 2.

The substantial equivalent activity includes a proteolytic activity (e.g. activity of proteases such as proteinases, peptidases, etc.), a binding activity to $Ca^{2+}$.

Examples of the nucleotide sequence hybridizing to the nucleotide sequence represented by SEQ ID NO. 5 or SEQ ID NO. 6 are (1) a nucleotide sequence of not less than about 70%, preferably not less than about 80%, more preferably not less than about 90%, for still better result, not less than about 95% identity to the nucleotide sequence represented by SEQ ID NO. 5, (2) a nucleotide sequence of not less than about 70%, preferably not less than about 80%, more preferably not less than about 90%, for still better result, not less than about 95% identity to the nucleotide sequence represented by SEQ ID NO. 6.

The hybridization can be carried out by the per se known method such as the method described in Molecular Cloning, 2nd (J. Sambrook et al., Cold Spring Harbor Lab. Press, 1989) and so on. When a commercially available library is used, the hybridization can be carried out in accordance with the instructions given in the accompanying manual, and particularly, be carried out in a highstringent condition.

In the highstringent condition, $Na^+$ concentration is at about 19 to 40 mM, preferably about 19 to 20 mM and a temperature is at about 50 to 70° C., preferably about 60 to 65° C. Particularly, the condition at about 19 mM of $Na^+$ and about 65° C. are preferred.

Preferable examples of the DNA coding for the protein represented by SEQ ID NO. 1 are a DNA comprising the nucleotide sequence represented by SEQ ID NO. 5. Preferable examples of the DNA coding for the protein represented by SEQ ID NO. 2 are a DNA comprising the nucleotide sequence represented by SEQ ID NO. 6 (FIG. 1).

The DNA coding for the partial peptide of the present invention may be any DNA comprising a nucleotide sequence encoding the partial peptide of the present invention as mentioned above. It may also be any one of genomic DNA, genomic DNA library, CDNA derived from the tissues or cells as mentioned above, cDNA library derived from the tissues or cells as mentioned above, and synthetic DNA.

Examples of DNA coding for the partial peptide of the present invention are (1) a DNA comprising a partial nucleotide sequence of DNA which comprises a nucleotide sequence represented by SEQ ID NO. 5, or a DNA comprising a partial nucleotide sequence of DNA which comprises a nucleotide sequence hybridizing under highstringent to the nucleotide sequence represented by SEQ ID NO. 5 condition and codes for a protein having a substantial equivalent activity to the protein comprising the amino acid sequence represented by SEQ ID NO. 1, (2) a DNA comprising a partial nucleotide sequence of DNA which comprises a nucleotide sequence represented by SEQ ID NO. 6, or a DNA comprising a partial nucleotide sequence of DNA which comprises a nucleotide sequence hybridizing under highstringent to the nucleotide sequence represented by SEQ ID NO. 6 condition and codes for a protein having a substantial equivalent activity to the protein comprising the amino acid sequence represented by SEQ ID NO. 2.

Preferable examples of DNA coding for the partial peptide of the present invention are (1) a DNA comprising a nucleotide sequence represented by SEQ ID NO. 7, or a DNA which comprises a nucleotide sequence hybridizing under highstringent condition to the nucleotide sequence represented by SEQ ID NO. 7 and codes for a partial peptide having a substantial equivalent activity to the protein of the present invention, (2) a DNA comprising a nucleotide sequence represented by SEQ ID NO. 8, or a DNA which comprises a nucleotide sequence hybridizing under highstringent condition to the nucleotide sequence represented by SEQ ID NO. 8 and codes for a partial peptide having a substantial equivalent activity to the protein of the present invention.

The method for hybridization and the highstringent condition have same meanings as mentioned above.

Preferable examples of the DNA coding for the partial peptide represented by SEQ ID NO. 3 are a DNA comprising the nucleotide sequence represented by SEQ ID NO. 7 and so on. Preferable examples of the DNA coding for the protein represented by SEQ ID NO. 4 are a DNA comprising the nucleotide sequence represented by SEQ ID NO. 8 and so on.

The DNA encoding the entire protein or the partial peptide of the present invention can be cloned either by PCR amplification using synthetic DNA primers having a partial nucleotide sequence of the DNA coding for the protein or by hybridization using the DNA inserted in a suitable vector and labeled with a DNA fragment comprising a part or full region of the protein or a synthetic DNA. The hybridization can be carried out by the method described in Molecular Cloning, 2nd (J. Sambrook et al., Cold Spring Harbor Lab. Press, 1989). When a commercially available DNA library is used, the instructions given in the accompanying manual can be followed.

The substitution of the nucleotide sequence of the DNA can be carried out by the per se known method such as Gapped duplex method, Kunkel method and so on by using the known kits such as Mutant™-G (Takara corporation), Mutant™-K (Takara corporation) and so on.

The cloned DNA coding for the protein of the present invention can be used directly or after digestion with a restriction enzyme or after addition of a linker depending on purposes. This DNA may have ATG as the translation initiation codon at the 5' end and TAA, TGA, or TAG as the termination codon at the 3' end. The translation initiation and termination codons can be added by means of suitable DNA adapters.

An expression vector for the protein of the present invention can be produced by, for example, (a) cutting out an objective DNA fragment from the DNA for the protein of the present invention and (b) ligating the objective DNA fragment with the downstream side of a promoter in a suitable expression vector.

The vector may include plasmids derived from *Escherichia coli*, e.g., pBR322, pBR325, pUC12, pUC13, etc.; plasmids derived from *Bacillus subtilis*, e.g., pUB110, pTP5, pC194, etc.; plasmids derived from yeasts e.g., pSH19, pSH15, etc.; bacteriophages such as λ-phage: animal virus such as retrovirus, vaccinia virus, etc.; insect virus; and other vecters such as pA1-11, pXT1, pRc/CMV, pRc/RSV, pcDNAI/Neo and so on.

According to the present invention, any promoter can be used as long as it is appropriate for the host cell which is used for expressing a gene. When the host is an animal cell, the promoter include AOX1 promoter, SV40 promoter, LTR promoter, CMV promoter, HSV-TK promoter, etc., and CMV promoter and SRd promoter are preferably used. When the host for the transformation is *Escherichia coli*, the promoter are preferably trp promoter, lac promoter, recA promoter, $\lambda_{PL}$ promoter, lpp promoter, T7 promoter, etc. When the host for the transformation is Bacillus, the promoter are preferably SPO1 promoter, SPO2 promoter, penP promoter, etc. When the host is a yeast, the promoter are preferably PHO5 promoter, PGK promoter, GAP promoter, ADH promoter, AOX1 promoter, etc. When the host is an insect cell, the promoter include polyhedrin promoter, P10 promoter, etc.

The expression vectors may, if necessary, further comprise enhancers, splicing signals, polyadenylation signals, selective markers, SV40 duplicate origin (hereinafter referred to as SV40 ori). Examples of selective markers are dihydrofolic acid reductase gene (hereinafter referred to as dhfr gene), neomycin-resistant gene (hereinafter referred to as Neo, G418 resistant) and so on. Particularly, when the dhfr gene is used as a selective marker against gene-deficient chinese hamster cell lines, cells transfected by the objective gene can be selected in a thymidine-free medium.

Furthermore, an appropriate signal sequence for a host can be added to the N-terminal side of the protein. When the host is *Escherichia coli*, the utilizable signal sequences may include PhoA signal sequence, OmpA signal sequence, etc. When the host is Bacillus, they may include α-amylase signal sequence, subtilisin signal sequence, etc. When the host is a yeast, they may include MFα signal sequence, SUC2 signal sequence, etc. When the host is an animal cell, they may include insulin signal sequence, α-interferon signal sequence, antibody molecule signal sequence, etc.

A transformant or transfectant is produced by using the vector thus constructed, which carries the DNA coding for the protein of the present invention.

The host may be, for example, Escherichia species, Bacillus species, yeast cells, insect cells, insects, animal cells, etc.

Examples of Escherichia species include *Escherichia coli* K12·DH1 (Proceedings of the National Academy of Sciences of the United State of America, Vol. 60, 160 (1968)), JM103 (Nucleic Acids Research, Vol. 9, 309 (1981)), JA221 (Journal of Molecular Biology, Vol. 120, 517 (1978)), HB101 (Journal of molecular Biology, Vol, 41, 459 (1969)), C600 (Genetics, Vol. 39, 440 (1954)), etc.

Examples of Bacillus species are, for example, *Bacillus subtilis* MI114 (Gene, Vol. 24, 255 (1983)), 207–21 (Journal of Biochemistry, Vol. 95, 76 (1984)), etc.

Examples of yeast cells are, for example, *Saccharomyces cerevisiae* AH22, AH22R⁻, NA87-11A, DKD-5D or 20B-12, *Schizosaccharomyces pombe* NCYC1913 or *Pichia pastoris*, etc.

Examples of insect cells are, for example, Spodoptera frugiperda cell (Sf cell), MG1 cell derived from center intestine of Trichoplusia ni, High Five™ cell derived from eggs of Trichoplusia ni, Mamestra brassicae-derived cell, Estigmena acrea-derived cell and so on when virus is AcNPV; and Bombyx mori N cell (BmN cell) and so on when virus is BmNPV. Examples of the Sf cell are, for example, Sf9 cell (ATCC CRL 1711), Sf21 cell (both, Vaughn J. L. et al., In Vivo, 13, 213–217(1977)) and so on.

Examples of insects include a larva of silkworm (*Bombyx mori* larva) (Maeda et al., Nature, 315, 592(1985)).

Examples of animal cells are, for example, monkey-derived COS-7 cell line, Vero, Chinese hamster ovary cell line (CHO cell), dhfr gene-deficient Chinese hamster cell line (CHO(dhfr⁻) cell), mouse L cell, mouse AtT-20, mouse myeloma cell, rat GH3, human FL, etc.

Depending on host cells used, transformation is done using standard techniques appropriate to such cells.

Transformation of Escherichia species can be carried out in accordance with methods as disclosed in, for example, Proceedings of the National Academy of Sciences of the United State of America, Vol. 69, 2110 (1972), and Gene, Vol. 17, 107 (1982), etc. Transformation of Bacillus species can be carried out in accordance with methods as disclosed in, for example, Molecular & General Genetics, Vol. 168, 111 (1979), etc. Transformation of yeast cells can be carried out in accordance with methods as disclosed in, for example, Methods in Enzymology, 194, 182–187(1991), etc. Transformation of insect cells or insects can be carried out in accordance with methods as disclosed in, for example, Bio/Technology, 6, 47–55, (1988). Transformation of animal cells can be carried out by methods as disclosed in, for example, Cell Engineering, separate vol. 8, New Cell Engineering Experiment Protocol, 263–267(1995) (Shujun Company) Virology, Vol. 52, 456 (1973), etc.

The transformants or transfectants wherein the expression vector carrying the DNA coding for the protein harbors can be obtained according to the aforementioned techniques.

Culture of the transformants (transfectants) of Escherichia or Bacillus species can be carried out suitably in a liquid culture medium. The culture medium may contains carbon sources, nitrogen sources, minerals, etc. which are necessary for growing the transformants. The carbon sources may include glucose, dextrin, soluble starch, sucrose, etc. The nitrogen sources may include organic or inorganic substances such as ammonium salts, nitrates, corn steep liquor, peptone, casein, meat extracts, bean-cakes, potato extracts, etc. Examples of the minerals may include calcium chloride, sodium dihydrogen phosphate, magnesium chloride, etc. It is further allowable to add yeasts, vitamines, growth-promoting factors, etc. It is suitable that the 6H of culture medium is at about 5 to 8.

The culture medium for Escherichia species is, for example, preferably M9 medium which contains glucose and casamino acid (Miller, Journal of Experiments in Molecular Genetics, 431–433, Cold Spring Harbor Laboratory, New York, (1972)). If necessary, drugs such as 3β-indolyl acrylic acid can be added to the medium to improve efficiency of the promoter. In the case of Escherichia organisms as a host, the culture is carried out usually at about 15 to 43° C. for about 3 to 24 hours. As required, aeration and stirring may be applied. In the case of Bacillus organisms as a host, the culture is carried out usually at about 30 to 40° C. for about 6 to 24 hours. As required, aeration and stirring may also be applied.

In the case of yeast transformants, the culture medium used may include, for example, Burkholder minimum medium (Bostian, K. L. et al., Proceedings of the National Academy of Sciences of the United State of America, Vol. 77, 4505 (1980)), SD medium containing 0.5% casamino acid (Bitter, G. A. et al., Proceedings of the National Academy of Sciences of the United State of America, Vol. 81, 5330 (1984)), etc. It is preferable that the pH of the culture medium is adjusted to be from about 5 to 8. The culture is carried out usually at about 20 to 35° C. for about 24 to 72 hours. As required, aeration and stirring may be applied.

In the case of the transformants of insects, the culture medium used may include the Grace's insect medium supplemented with additives such as inactivated 10% bovine serum (Grace, T. C. C., Nature, 195, 788 (1962)). It is preferable that the pH of the culture medium is adjusted to be about 6.2 to 6.4. The culture is usually carried out at about 27° C. for about 3 to 5 days. As desired, aeration and stirring may be applied.

In the case of the transfectants of animal cells, the culture medium used may include MEM medium (Science, Vol. 122, 501 (1952)), DMEM medium (Virology, Vol. 8, 396 (1959)), RPMI 1640 medium (Journal of the American Medical Association, Vol. 199, 519 (1967)), 199 medium (Proceedings of the Society of the Biological Medicine, Vol. 73, 1 (1950)), etc. which are containing, for example, about 5 to 20% of fetal calf serum. It is preferable that the pH is from about 6 to 8. The culture is usually carried out at about 30 to 40° C. for about 15 to 60 hours. As required, medium exchange, aeration and stirring may be applied.

Separation and purification of the protein from the above-mentioned cultures can be carried out according to methods described herein below.

To extract the protein from the cultured microorganisms or cells, the microorganisms or cells are collected by known methods after the culture, suspended in a suitable buffer solution, disrupted by ultrasonic waves, lysozyme and/or freezing and thawing, etc. and, then, a crude protein extract is obtained by centrifugation or filtration. Other conventional extraction or isolation methods can be applied. The buffer solution may contain a protein-denaturing agent such as urea or guanidine hydrochloride or a surfactant such as Triton X-100™.

In the case where proteins are secreted into culture media, supernatants are separated from the microorganisms or cells after culture and collected by known methods. The culture supernatant containing the protein can be purified by suitable combinations of known methods for separation, isolation and purification. The known methods of separation, isolation and purification may include methods which utilizes solubility, such as salting out or sedimentation with solvents, methods which utilizes chiefly a difference in the molecular size or weight, such as dialysis, ultrafiltration, gel filtration and SDS-polyacrylamide gel electrophoresis, methods utilizing a difference in the electric charge, such as ion-exchange chromatography, methods utilizing specific affinity such as affinity chromatography, methods utilizing a difference in the hydrophobic property, such as reversed-phase high-performance liquid chromatography, and methods utilizing a difference in the isoelectric point such as isoelectric electrophoresis, etc.

In cases where the protein thus obtained is in a free form, the free protein can be converted into a salt thereof by known methods or method analogous thereto. In case, where the protein thus obtained is in a salt form vice versa, the protein salt can be converted into a free form or into any other salt thereof by known methods or method analogous thereto.

The protein produced by the transformant can be arbitrarily modified or a polypeptide can be partly removed therefrom, by a suitable enzyme before or after the purification. The enzyme may include trypsin, chymotrypsin, arginyl endopeptidase, protein kinase, glycosidase, etc. The amount of the protein of the present invention thus obtaine can be measured by binding assay with a labeled ligand or by enzyme immunoassays (enzyme linked immunoassays) using specific antibodies.

The antibodies against the protein of the present invention, its partial peptide or a salt of either of them are any antibodies such as polyclonal antibodies and monoclonal antibodies which can recognize the protein of the present invention, its partial peptide or their salts.

The antibodies against the protein of the present invention, its partial peptide or a salt of either of them (hereinafter referred to as the protein of the present invention) may be manufactured by methods per se known to those of skill in the art or methods similar thereto, using the protein as antigen. For example, polyclonal antibodies can be manufactured by the method as given below.

[Preparation of Monoclonal Antibody]

(a) Preparation of Monoclonal Antibody-Producing Cells.

The protein of the present invention is administered to warm-blooded animals either solely or together with carriers or diluents to the site favorable for antibody production. In order to potentiate the antibody productivity upon the administration, complete Freund's adjuvants or incomplete Freund's adjuvants may be administered. The administration is usually carried out once every two to six weeks and two to ten times in total. Examples of the applicable warm-blooded animals are monkeys, rabbits, dogs, guinea pigs, mice, rats, sheep, goats and chickens. The use of mice and rats is preferred.

In establishing cells which produce monoclonal antibodies, an animal with the detectable antibody titer is selected from animals (e.g. mice) immunized with antigens, then spleen or lymph node is collected after two to five days from the final immunization and antibody-producing cells contained therein are fused with myeloma cells to obtain monoclonal antibody-producing hybridomas. Measurement of the antibody titer in antisera may, for example, be carried out by reacting a labeled protein (which will be mentioned later) with the antiserum followed by measuring the binding activity of the labeling agent with the antibody. The cell fusion may be carried out, for example, by a method of Koehler and Milstein (Nature, 256, 495, 1975), Examples of the fusion accelerator are polyethylene glycol (PEG), Sendai virus, etc. and the use of PEG is preferred.

Examples of the myeloma cells are NS-1, P3U1, SP2/0, AP-1, etc. and the use of P3U1 is preferred. The preferred fusion ratio of the numbers of antibody-producing cells used (spleen cells) to the numbers of myeloma cells is within a range of about 1:1 to 20:1. When PEG (preferably, PEG 1000 to PEG 6000) is added in a concentration of about 10–80% followed by incubating at 20–40° C. (preferably, at 30–37° C.) for one to ten minutes, an efficient cell fusion can be carried out.

Various methods may be applied for screening a hybridoma which produces a monoclonal antibody. For example, a supernatant of hybridoma culture is added to a solid phase (e.g. microplate) to which the protein antigen is adsorbed either directly or with a carrier, then anti-immunoglobulin antibody (anti-mouse immunoglobulin antibody is used when the cells used for the cell fusion are those of mouse) which is labeled with a radioactive substance, an enzyme or the like, or protein A is added thereto and then monoclonal antibodies bound on the solid phase are detected; or a supernatant liquid of the hybridoma culture is added to the solid phase to which anti-immunoglobulin or protein A is adsorbed, then the protein labeled with a radioactive substance or an enzyme is added and monoclonal antibodies bound with the solid phase is detected.

Selection and cloning of the monoclonal antibody-producing hybridoma may be carried out by methods per se known to those of skill in the art or methods similar thereto. Usually, it is carried out in a medium for animal cells, containing HAT (hypoxanthine, aminopterin and thymidine). With respect to a medium for the selection, for the cloning and for the growth, any medium may be used so far as hybridoma is able to grow therein. Examples of the medium are an RPMI 1640 medium (Dainippon Pharmaceutical Co., Ltd., Japan) containing 1–20% (preferably 10–20%) of fetal calf serum (FCS), GIT medium (Wako Pure Chemical, Japan) containing 1–20% of fetal calf serum and a suitable serum-free medium for hybridoma (SFM-101; Nissui Seiyaku, Japan). The culture temperature is usually 20–40° C. and, preferably, about 37° C. The culture period is usually from five days to three weeks and, preferably, one to two weeks. The culture is usually carried out in 5% carbon dioxide gas. The antibody titer of the supernatant of the hybridoma culture may be measured by the same manner as in the above-mentioned measurement of the antibody titer in the antiserum.

(b) Purification of the Monoclonal Antibody.

The separation and purification of the monoclonal antibody may be carried out by methods for separating/purifying immunoglobulin such as salting-out, precipitation with alcohol, isoelectric precipitation, electrophoresis, adsorption/deadsorption using ion exchangers such as DEAE, ultracentrifugation, gel filtration, specific purifying methods in which only an antibody is collected by treatment with an active adsorbent such as an antigen-binding solid phase, protein A or protein G and the bond is dissociated whereupon the antibody is obtained.

[Preparation of a polyclonal antibody]

The polyclonal antibody of the present invention can be produced by per se known methods or methods analogous thereto. The method comprises preparing a complex of immunogen (antigen protein) and carrier protein, immunizing a warm-blooded animal in the same manner as described for the production of the monoclonal antibody, harvesting a fraction containing the antibody against the protein of the invention from the immunized animal, and purifying the harvested antibody.

Referring to the immunogen-carrier protein conjugate for use in the immunization of a warm-blooded animal, the kind of carrier protein and the ratio of the carrier and hapten are not particularly restricted only if the production of the antibody against the hapten conjugated with the particular carrier protein and used for immunization proceeds efficiently. Thus, for example, bovine serum albumin, bovine thyroglobulin, hemocyanine, or the like is coupled in the weight ratio of about 0.1 to 20, preferably about 1 to about 5, to unity of the hapten.

A variety of condensing agents can be used for this coupling between the hapten and the carrier. Thus, for example, a glutaraldehyde, carbodiimide, maleimide, or a thiol or dithiopyridyl group-containing active ester reagent can be employed.

The condensation reaction product is administered to a warm-blooded animal at a site favorable for antibody production, either as it is alone or together with a carrier or diluent. Enhancing antibody production, complete Freund's adjuvant or incomplete Freund's adjuvant may be administered. Administration is carried out generally once in about 2–6 weeks for a total of about 3–10 times.

The polyclonal antibody can be harvested from the blood, ascites fluid, or other body fluid, preferably from the blood, of the host warm-blooded animal.

The polyclonal antibody titer in the antiserum can be determined in the same manner as the determination of monoclonal antibody described hereinbefore. The separation and purification of the polyclonal antibody can be carried out by the same method as that described for the separation and purification of monoclonal antibody.

The antisense DNA having a substantial complementary nucleotide sequence to the DNA coding for the protein of the invention or the partial peptide (hereinafter referred to as the DNA of the invention) can be any antisense DNA having a nucleotide sequence complementary to that of the DNA of the present invention and capable of suppressing expression of the DNA.

The substantial complementary nucleotide sequence may, for example, be a nucleotide sequence having a identity of not less than about 70%, preferably not less than about 80%, and for still better results, not less than about 90% to the total nucleotide sequence or partial nucleotide sequence of the nucleotide sequence complementary to that of the DNA of the present invention. Particularly preferred is an antisense DNA having a identity of not less than about 70%, preferably not less than about 80%, and more preferably not less than about 90% to the nucleotide sequence complementary to that of the domain, of the complete nucleotide sequence of the DNA of the invention, which encodes the N-terminal region of the protein of the present invention (e.g. the nucleotide sequence of the domain around the initiation codon). The antisense DNA can be synthesized using a known DNA synthesis hardware.

The protein of the present invention is a calpain (preferably human calpain) with a molecular weight of about 7 to $9 \times 10^4$ Da, preferably about $8 \times 10^4$ Da. It has a proteolytic activity which is regulated by intracellular calcium concentration and cleaves intracellular proteins (e.g. cytoskeletal proteins such as fodrins, enzyme proteins such as kinases, transcription factors, cytokines, etc.) in accordance with the calcium-associated transmission of information. Furthermore, the protein stability solubility can be improved by adding a small subunit of calpain, connectin (The Journal of Biological Chemistry, 270, No. 52, 9931158-31162, 1995), or the like in combination with the protein of the present invention.

Examples of the small subunit of calpain are a known human calpain small subunit comprising the amino acid sequence represented by SEQ ID NO:9 (FIG. 2) or any novel small subunit that would be discovered in the future.

The small subunit of calpain can be prepared by the above-mentioned recombinant DNA technique utilizing a known DNA coding for the small subunit of calpain, for example, the DNA comprising a nucleotide sequence represented by SEQ ID NO:10 (FIG. 2).

Uses for the protein of the present invention, its partial peptide, a salt of either of them (all of which are sometimes referred to as the protein of the present invention), the DNA coding for the protein of the present invention or its partial peptide thereof (hereinafter sometimes referred to as the DNA of the present invention), and the antibody against the protein of the present invention (hereinafter sometimes referred to as the antibody of the present invention), and the antisense DNA are now described.

(1) Therapeutic and prophylactic composition for the diseases with which the protein of the present invention is associated Since the protein of the present invention has the characteristics of calpain such as an intracellular $Ca^{2+}$-activated proteolytic activity, etc., and cleaves intracellular proteins (e.g. cytoskeletal proteins such as fodrins; enzyme proteins such as kinases; transcription factors; cytokines; etc.), a variety of diseases associated with abnormal calpain expression such as cancer, cerebral apoplexy, cerebral infarction, subarachnoid hemorrhage, Alzheimer's disease, myodystrophy, cataract, ischemic heart disease, atherosclerosis, arthritis, collagen disease, for example develop when an abnormality or defect occurs in the protein of the present invention or in the DNA of the present invention, or when the level of expression thereof is decreased or elevated, or when the intracellular $Ca^{2+}$ ion concentration elevates.

Therefore, the protein or the DNA of the present invention can be used as a pharmaceutical composition such as a therapeutic or prophylactic composition for various diseases such as cancer, cerebral apoplexy, cerebral infarction, subarachnoid hemorrhage, Alzheimer's disease, myodystrophy, cataract, ischemic heart disease, atherosclerosis, arthritis, and collagen disease.

For example, when there is a patient whose signal transductions in cells cannot function sufficiently or normally because of a decrease or a defect in the protein of the present invention in vivo, the role of the protein of the present invention for said patient can be expected sufficiently or normally by:

(a) administering the DNA coding for the protein of the present invention to the patient to express it;

(b) inserting the DNA coding for the protein of the present invention into cells to express it and transplanting the cells to said patient, or (c) administering the protein to the patient.

When the DNA of the present invention is used as the above-mentioned pharmaceutical composition, said DNA may be used alone or after inserting it into a suitable vector such as retrovirus vector, adenovirus vector, adenovirus-associated virus vector, pox virus etc. followed by subjecting the product vector to a conventional means. The DNA can also be administered as "naked" DNA, with adjuvants to assist in uptake, by "gene" gun or by a catheter such as a catheter with a hydrogel.

If one would wishes to use the protein of the present invention, one would use it in a purified form, preferably at least 90% pure, more preferably at least 95% pure, still more preferably at least 98% pure and most preferably at least 99% pure.

For example, the protein or the DNA of the present invention can be used orally in the form of tablets which may be sugar coated as necessary, capsules, elixirs, microcapsules etc., or non-orally in the form of injectable preparations such as aseptic solutions and suspensions in water or other pharmaceutically acceptable liquids. These preparations can be produced by mixing the protein or DNA of the present invention with physiologically acceptable carriers, flavoring agents, excipients, vehicles, antiseptics, stabilizers, binders etc. in unit dosage forms required for generally accepted manners of pharmaceutical making. Active ingredient contents in these preparations are set so that an appropriate dose within the specified range is obtained.

Additives which can be mixed in tablets, capsules etc. include binders such as gelation, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is the capsule, the above-mentioned materials may further incorporate liquid carriers such as oils and fats. Sterile compositions for injection can be formulated by ordinary methods of pharmaceutical making such as by dissolving or suspending active ingredients, naturally occurring vegetable oils such as sesame oil and coconut oil, etc. in vehicles such as water for injection to create pharmaceutical compositions.

Aqueous liquids for injection include physiological saline and isotonic solutions containing glucose and other auxiliary agents, e.g., D-sorbitol, D-mannitol and sodium chloride, and may be used in combination with appropriate dissolution aids such as alcohols, e.g., ethanol, polyalcohols, e.g., propylene glycol and polyethylene glycol, nonionic surfactants, e.g., polysorbate 80™ and HCO-50 etc. oily liquids include sesame oil and soybean oil, and may be used in combination with dissolution aids such as benzyl benzoate and benzyl alcohol. Furthermore the above-mentioned materials may also be formulated with buffers, e.g., phosphate buffer and sodium acetate buffer; soothing agents, e.g., benzalkonium chloride, procaine hydrochloride; stabilizers, e.g., human serum albumin, polyethylene glycol; preservatives, e.g., benzyl alcohol, phenol; antioxidants etc. The thus-prepared pharmaceutical composition such as an injectable liquid is normally filled in an appropriate ampule.

Because the thus-obtained preparation is safe and of low toxicity, it can be administered to humans or mammals (e.g., rats, rabbits, sheep, pigs, bovines, cats, dogs, monkeys, etc.).

The dose of the protein or DNA is normally about 0.1–100 mg, preferably about 1.0–50 mg, and more preferably about 1.0–20 mg per day for an adult (weighing 60 kg) in oral administration, depending on symptoms etc. In non-oral administration, it is advantageous to administer the protein or DNA in the form of injectable preparation at a daily dose of about 0.01–30 mg, preferably about 0.1–20 mg, and more preferably about 0.1–10 mg per administration by an intravenous injection for an adult (weighing 60 kg), depending on subject of administration, target organ, symptoms, method of administration etc. For other animal species, corresponding does as converted per 60 kg weight can be administered.

(2) Screening of compounds as candidates which are medicinally useful against diseases The protein of the present invention is associated with the down-regulation of protein kinase C which controls cell growth and has the activity to cause cell death known as apoptosis. Therefore, any compounds or their salts which activates the function (e.g. proteolytic activity, etc.) of the protein of the present invention can be utilized as a therapeutic or prophylactic composition for cancer, etc.

Meanwhile, the protein of the present invention has a proteolytic activity to decompose intracellular proteins (e.g. cytoskeletal proteins such as fodrins; enzyme proteins such as kinases; transcription factors; and cytokines) and, therefore, any compounds or their salts that inhibit the function (e.g. proteolytic activity, etc.) of the protein of the present invention can be used as a therapeutic and prophylactic composition for diseases involving destruction of cells and cellular components (e.g., cerebral apoplexy, cerebral infarction, subarachnoid hemorrhage, Alzheimer's disease, myodystrophy, cataract, ischemic heart disease, atherosclerosis, arthritis, collagen disease, etc.).

Therefore, the protein of the present invention is useful as a screening reagent for compounds or their salts which would activate or inhibit the function of the protein of the present invention.

The present invention thus provides (1) a method for screening for a compound which activates the function (e.g. proteolytic activity, etc.) of the protein of the present invention or its partial peptide, or a salt of either of them [such compounds will sometimes be referred to as activator], or a compound which inhibits the function of the protein of the present invention or its partial peptide, or a salt of either of them [such compounds will sometimes be referred to as inhibitor] characterized in that the protein of the present invention or its partial peptide, or a salt of either of them, is used as a screening reagent.

More particularly, the invention provides (2) a method for screening for the activator or inhibitor, which comprises comparing the results in cases of (i) a substrate is contacted with the protein of the present invention and (ii) a substrate and a test compound are contacted with the protein of the present invention.

More specifically, the above screening method is characterized by measuring and comparing the proteolytic activity (e.g. activity of proteases such as proteinases, peptidases, etc.) of the protein of the present invention in cases of (i) and (ii).

The substrate may include any substances which may function as substrates for the protein of the present invention. Examples of the substrate are casein, azocasein, FITC-casein, radio(e.g. $^{14}$C, $^{3}$H, etc.) labeled casein, collagen, azocollagen, FITC-collagen, radio($^{14}$C, $^{3}$H, etc.)-labeled collagen, and oligopeptides having a (7-methoxycoumarin-4-yl)acetyl group in the N-terminal domain and an $N^{3}$-(2, 4-dinitrophenyl)-2,3-diaminopropionyl group in the position a few residues removed from said domain towards the C-terminus.

Examples of the test compound are peptides, proteins, nonpeptide compounds, synthetic compounds, fermentation products, cell extracts, plant extracts, and animal tissue extracts. Such compounds may be novel compounds or known compounds.

For carrying the above screening method into practice, the protein of the present invention is first suspended in a suitable screening buffer to prepare a sample. The buffer may be any buffer that does not affect the binding of the protein of the present invention to the substrate, such as phosphate buffer or Tris-HCl buffer in the pH range of about 4–10 (preferably pH about 6–8).

The proteolytic activity of the protein of the present invention can be determined in accordance with the known assay protocols for proteolytic activity, for example, the procedures described in, *inter alia*, Seibutsu Kagaku Jikkenho, Proteolytic Enzyme I (Biochemical Experiment Protocols, Proteolytic Enzyme I) published by Gakkai Shuppan Center, at pages 57–76. Specifically, any test compounds that activate the proteolytic activity, etc. by not less than about 20%, preferably not less than about 30%, more preferably not less than about 50%, in experiment (ii) as compared with experiment (i) can be selected as an activator of the proteolytic activity of the protein of the present invention, while any test compounds that inhibit the proteolytic activity, etc. by not less than about 20%, preferably not less than about 30%, more preferably not less than about 50%, in experiment (ii) as compared with experiment (i) can be selected as an inhibitor of the proteolytic activity of the protein of the present invention.

The screening kit of the present invention comprises the protein of the present invention, its partial peptide, or a salt of either of them. The following is an example of screening kit principle of the present invention.

[Screening reagents]

(1) Screening Buffer 1M Tris-HCl Buffer, pH 7.5

(2) Protein Sample

The protein of the present invention, its partial peptide or a salt of either of them (3) Substrate solution (e.g. casein solution)

Dissolve 1.5 g of casein (Merck, Wako Pure Chemical) in the screening buffer (pH 7.5) to make 50 ml. Preferably, distribute the solution in 1 ml aliquots and store them frozen.

(4) Substrate solution for the assay

Add 60 $\mu$l of 1 M $CaCl_2$ and 10 $\mu$l of 2-mercapto-ethanol (2-ME) to 3 ml of casein solution and dilute the mixture with sufficient distilled water to make 30 ml. For control, add 0.5 M EDTA solution instead of 1 M $CaCl_2$. These solutions can be stored frozen but it is recommended that they should be prepared afresh at intervals of about 2 weeks. The final concentrations of the substrate solution are 3 mg/ml casein, 2 mM $CaCl_2$, 5 mM 2-ME in 0.1 M Tris-HCl (pH 7.5).

(5) Detection Absorbance at 280 nm

[Assay protocol]

After incubating the substrate solution (0.5 ml) at 30° C. for 5 min., add a calpain solution (0.5–5 $\mu$g as calpain), and react at 30° C. for 20 min. Add 0.5 ml of 10% trichloroacetic acid (TCA) so as to stop the reaction, allow the reaction mixture to stand at 4° C. for 15 min., and centrifuge at 3,000×g for 5 min. Perform a control reaction using a calcium-free substrate solution, and determine the calcium-dependent increase in the absorbance of the supernatant at 280 nm as a proteolytic activity of calpain.

If the absorbance at 280 nm is increased due to addition of the test compound, the substance is regarded as an activator of the proteolytic activity of the protein of the present invention. Conversely if the absorbance at 280 nm is decreased upon addition of the test compound, the substance is regarded as an inhibitor of the proteolytic activity of the protein of the present invention.

The compound or a salt thereof which can be identified by the screening method of the present invention or by using the screening kit of the present invention is a compound selected from among a peptide, protein, nonpeptide compound, synthetic compound, fermentation product, cell extract, plant extract, or animal tissue extract, which activates or inhibits the function of the protein of the present invention.

The salt of the compound may be the same those as mentioned above for the protein of the present invention.

The compound which activates the function of the protein of the present invention is safe and of low toxic therapeutic and prophylactic composition for various diseases such as cancer, for example.

On the other hand, the compound which inhibits the function of the protein of the present invention is safe and of low toxic therapeutic and prophylactic composition for various diseases such as cerebral apoplexy, cerebral infarction, subarachnoid hemorrhage, Alzheimer's disease, myodystrophy, cataract, ischemic heart disease, atherosclerosis, arthritis, and collagen disease.

The compound which is identified by the screening method or the screening kit can be used as the above-mentioned therapeutic or prophylactic composition in accordance with a conventional means. The compound can be used in the form of tablets, capsules, elixirs, microcapsules, aseptic solutions, suspensions and so on as well as the pharmaceutical composition comprising the protein or the DNA of the present invention as mentioned above.

Because the thus-obtained preparation is safe and of low toxicity, it can be administered to humans or mammals (e.g., rats, rabbits, sheep, pigs, bovines, cats, dogs, monkeys, etc.).

The dose of the compound is normally about 0.1–100 mg, preferably about 1.0–50 mg, and more preferably about 1.0–20 mg per day for an adult (weighing 60 kg) in oral administration, depending on symptoms etc. In non-oral administration, it is advantageous to administer the compound in the form of injectable preparation at a daily dose of about 0.01–30 mg, preferably about 0.1–20 mg, and more preferably about 0.1–10 mg per administration by an intravenous injection for an adult (weighing 60 kg), depending on subject of administration, target organ, symptoms, method of administration etc. For other animal species, corresponding does as converted per 60 kg weight can be administered.

(3) Quantitative Determination of the Protein of the Present Invention

The antibody of the present invention is capable of specifically recognizing the protein of the present invention and, accordingly, it can be used for a quantitative determination of the protein of the present invention in test liquid samples and particularly for a quantitative determination by sandwich immunoassays.

Thus, the present invention provides, for example, the following methods:

(i) a quantitative determination of the protein of the present invention in a test liquid sample, which comprises (a) competitively reacting the test liquid sample and a labeled protein of the present invention with the antibody of the present invention, and (b) measuring the ratio of the labeled protein of the present invention binding with said antibody; and (ii) a quantitative determination of the protein of the present invention in a test liquid sample, which comprises (a) reacting the test liquid sample with an antibody immobilized on an insoluble carrier and a labeled antibody simultaneously or continuously, and (b) measuring the activity of the labeling agent on the insoluble carrier, wherein one antibody is capable of recognizing the N-terminal region of the protein of the present invention while another antibody is capable of recognizing the C-terminal region of the protein of the present invention.

When the monoclonal antibody of the present invention recognizing a protein of the present invention (hereinafter, may be referred to as "monoclonal antibody of the present invention") is used, the quantity of the protein of the present invention can be measured and, moreover, the protein of the present invention can be detected by means of a tissue staining, etc. as well. For such an object, antibody molecules per se may be used or $F(ab')_2$, Fab' or Fab fractions of the antibody molecule may be used too. There is no particular limitation for the measuring method using the antibody of the present invention and any measuring method may be used so far as it relates to a method in which the amount of antibody, antigen or antibody-antigen complex, depending on or corresponding to the amount of antigen, e.g. the amount of the protein of the present invention in the liquid sample to be measured, is detected by a chemical or a physical means and then calculated using a standard curve prepared by a standard solution containing the known amount of antigen. For example, nephrometry, competitive method, immunometric method and sandwich method are suitably used and, in terms of sensitivity and specificity, the sandwich method which will be described herein later is particularly preferred.

Examples of the labeling agent used in the measuring method using the labeling substance are radioisotopes, enzymes, fluorescent substances, luminescent substances, colloids, magnetic substances, etc. Examples of the radioisotope are [$^{125}$I], [$^{131}$I], [$^{3}$H] and [$^{14}$C]. Preferred examples of the enzyme are those which are stable and with much specific activity, such as β-galactosidase, β-glucosidase, alkali phosphatase, peroxidase and malate dehydrogenase. Examples of the fluorescent substance are fluorescamine, fluorescein isothiocyanate, etc. Examples of the luminescent substance are luminol, luminol derivatives, luciferin, lucigenin, etc. Further, a biotin-avidin system may also be used for binding an antibody or antigen with a labeling agent.

In an insolubilization (immobilization) of antigens or antibodies, a physical adsorption may be used or a chemical binding which is usually used for insolubilization or immobilization of proteins or enzymes may be used as well. Examples of the carrier are insoluble polysaccharides such as agarose, dextran and cellulose; synthetic resins such as polystyrene, polyacrylamide and silicone; glass; etc.

In a sandwich (or two-site) method, the test liquid is made to react with an insolubilized monoclonal antibody of the present invention (the first reaction), then it is made to react with a labeled monoclonal antibody of the present invention (the second reaction) and the activity of the labeling agent on the insoluble carrier is measured whereupon the amount of the protein of the present invention in the test liquid can be determined. The first reaction and the second reaction may be conducted reversely or simultaneously or they may be conducted with an interval. The type of the labeling agent and the method of insolubilization (immobilization) may be the same as those mentioned already herein. In the immunoassay by means of a sandwich method, it is not always necessary that the antibody used for the labeled antibody and the antibody for the solid phase is one type or one species but, with an object of improving the measuring sensitivity, etc., a mixture of two or more antibodies may be used too.

In the method of measuring the protein of the present invention by the sandwich method of the present invention, the preferred monoclonal antibodies of the present invention used for the first and the second reactions are antibodies wherein their sites binding to the protein of the present invention are different from each other. Thus, the antibodies used in the first and the second reactions are those wherein, when the antibody used in the second reaction recognizes the C-terminal region of the protein of the present invention, then the antibody recognizing the site other than C-terminal regions, e.g. recognizing the N-terminal region, is preferably used in the first reaction.

The monoclonal antibody of the present invention may be used in a measuring system other than the sandwich method such as a competitive method, an immunometric method and a naphrometry. In a competitive method, an antigen in the test solution and a labeled antigen are made to react with an antibody in a competitive manner, then an unreacted labeled antigen (F) and a labeled antigen binding with an antibody (B) are separated (i.e. B/F separation) and the labeled amount of any of B and F is measured whereupon the amount of the antigen in the test solution is determined. With respect to a method for such a reaction, there are a liquid phase method in which a soluble antibody is used as the antibody and the B/F separation is conducted by polyethylene glycol, a second antibody to the above-mentioned antibody, etc.; and a solid phase method in which an immobilized antibody is used as the first antibody or a soluble antibody is used as the first antibody while an immobilized antibody is used as the second antibody.

In an immunometric method, an antigen in the test solution and an immobilized antigen are subjected to a competitive reaction with a certain amount of a labeled antibody followed by separating into solid and liquid phases; or the antigen in the test solution and an excess amount of labeled antibody are made to react, then an immobilized antigen is added to bind an unreacted labeled antibody with the solid phase and separated into solid and liquid phases. After that, the labeled amount of any of the phases is measured to determine the antigen amount in the test solution.

In a nephrometry, the amount of insoluble sediment which is produced as a result of the antigen-antibody reaction in a gel or in a solution is measured. Even when the antigen amount in the test solution is small and only a small amount of the sediment is obtained, a laser nephrometry wherein scattering of laser is utilized can be suitably used.

In applying each of those immunological measuring methods (immunoassays) to the measuring method of the present invention, it is not necessary to set up any special condition, operation, etc. therefor. A measuring system (assay system) for the protein of the present invention may be constructed taking the technical consideration of the persons skilled in the art into consideration in the conventional conditions and operations for each of the methods. With details of those conventional technical means, a variety of reviews, reference books, etc. may be referred to. They are, for example, Hiroshi Irie (ed): "Radioimmunoassay" (Kodansha, Japan, 1974); Hiroshi Irie (ed): "Radioimmunoassay; Second Series" (Kodansha, Japan, 1979); Eiji Ishikawa et al. (ed): "Enzyme Immunoassay" (Igaku Shoin, Japan, 1978); Eiji Ishikawa et al. (ed): "Enzyme Immunoassay" (Second Edition) (Igaku Shoin, Japan, 1982); Eiji Ishikawa et al. (ed): "Enzyme Immunoassay" (Third Edition) (Igaku Shoin, Japan, 1987); "Methods in Enzymology" Vol. 70 (Immunochemical Techniques (Part A)); ibid. Vo. 73 (Immunochemical Techniques (Part B)); ibid. Vo. 74 (Immunochemical Techniques (Part C)); ibid. Vo. 84 (Immunochemical Techniques (Part D: Selected Immunoassays)); ibid. Vol. 92 (Immunochemical Techniques (Part E: Monoclonal Antibodies and General Immunoassay Methods)); ibid. Vol. 121 (Immunochemical Techniques (Part I: Hybridoma Technology and Monoclonal Antibodies)) (Academic Press); etc.

By using the antibody against the protein of the present invention in the above manner, the protein of the present invention can be assayed with high sensitivity.

In addition, by determining the concentration of the protein of the present invention by using the antibody against the protein of the present invention, various diseases such as cancer, cerebral apoplexy, cerebral infarction, subarachnoid hemorrhage, Alzheimer's disease, myodystrophy, cataract, ischemic heart disease, atherosclerosis, arthritis, collagen disease, etc. can be successfully diagnosed.

Furthermore, the antibody of the present invention can be used for the purpose of detecting the protein of the present invention which may be present in test samples such as body fluids or tissues. The antibody can also be used for the construction of an antibody column for purification of the protein of the present invention, detection of the protein of the present invention in the fractions in the course of purification, and analysis of the behavior of the protein of the present invention in the cell under investigation.

(4) Gene Diagnostic Agent

By using the DNA of the present invention as a probe, for instance, an abnormality (gene abnormality) of the DNA or mRNA coding for the protein of the present invention or its partial peptide in humans or mammals (e.g. rat, mouse, guinea pig, rabbit, sheep, swine, bovine, horse, cat, dog, monkey, chimpanzee, etc.) can be detected. Therefore, the DNA of the present invention is useful as a gene diagnostic agent for the damage to the DNA or mRNA, mutation thereof, or decreased expression thereof, or increased expression or overexpression of the DNA or mRNA.

The above-mentioned gene diagnosis using the DNA of the present invention can be carried out by, for example, the per se known Northern hybridization assay or PCR-SSCP assay (Genomics, 5, 874–879 (1989); Proceedings of the National Academy of Sciences of the United States of America, 86, 2766–2770 (1989)).

Decrease in expression of the DNA as found by Northern hybridization assay or a mutation of the DNA as detected by the PCR-SSCP assay may lead, with high probability, to the diagnosis of cancer, cerebral apoplexy, cerebral infarction, subarachnoid hemorrhage, Alzheimer's disease, myodystrophy, cataract, ischemic heart disease, atherosclerosis, arthritis, collagen disease, or the like.

(5) Antisense DNA

As mentioned above, the protein of the present invention can decompose intracellular proteins (e.g. cytoskeletal proteins such as fodrins, enzyme proteins such as kinases, transcription factors, cytokines, etc.). Therefore, an antisense DNA capable of complementary conjugation to the DNA of the present invention to suppress expression of the DNA is capable of inhibiting the function of the protein or the DNA of the present invention in the body. Therefore, the antisense DNA can be used as a therapeutic and prophylactic composition for diseases involving the destruction of cells and cellular components (such as cerebral apoplexy, cerebral infarction, subarachnoid hemorrhage, Alzheimer's disease, myodystrophy, cataract, ischemic heart disease, atherosclerosis, arthritis, collagen disease, etc.).

The antisense DNA can be used as the above-mentioned therapeutic and prophylactic composition as well as the pharmaceutical composition comprising the protein or the DNA of the present invention as mentioned above.

(6) Preparation of Non-human Animals Harboring a Foreign DNA Coding for the Protein of the Present Invention Transgenic non-human animals which express the protein of the present invention can be constructed by using the DNA of the present invention. As the species of non-human animals that can be used, a variety of mammals (e.g. rat, mouse, rabbit, sheep, swine, bovine, cat, dog, monkey, etc.), etc. (hereafterin referred to as animals) can be mentioned. Particularly preferred are the mouse and the rabbit.

In transferring the DNA of the present invention to a host animal, it is generally advantageous to use the DNA as a gene construct prepared by conjugating the DNA downstream of a promoter capable of expressing the DNA in animal cells. For the transfer of a rabbit-derived DNA of the invention, for instance, a DNA transgenic animal for high production of the protein of the present invention can be constructed by the microinjection of, for example, the fertilized rabbit egg with a gene construct prepared by conjugating the DNA of the present invention as derived from an animal having high homology therewith downstream of a promoter capable of causing the expression of the DNA of the present invention in animal cells. As for such promoters, viral promoters or ubiquitous expression promoters such as metallothionein promoter can also be used.

The transfer of the DNA in the fertilized egg cell stage is secured in all the germ and somatic cells of the host animal. The presence of the protein of the present invention in the germ cells of the DNA-transferred animal means that all the progeny of the transgenic animal invariably harbor the protein of the present invention in their germ and somatic cells. The offsprings of such an animal to which the gene has been passed on have the protein of the present invention in all of their germ and somatic cells.

The transgenic animal in which the DNA of the present invention has been expressed is confirmed to retain the gene stably by copulation and then can be bred from generation to generation as the DNA-harboring animals in the usual breeding environment. Furthermore, by mating male and female animals harboring the objective DNA, it is possible to obtain homozygotes having the introduced gene in both of the homologous chromosomes, and by mating such partners, it is possible to insure that all the progeny animals will harbor this DNA.

The animal to which the DNA of the present invention has been passed on has the protein of the present invention expressed in a high degree so that it is useful as an animal for screening for compounds and salts which would activate or inhibit the proteolytic activity of the protein of the present invention.

The animal to which the DNA of the present invention has been transferred can also be used as a source of cells for tissue culture. For example, the protein of the present invention can be studied either directly by analyzing the DNA or RNA in the tissues of a mouse to which the DNA of the present invention has been transferred or analyzing a tissue containing the protein of the present invention as expressed by the gene. It is possible to culture cells from a tissue containing the protein of the present invention by the standard tissue culture technique and, using the culture, study the functions of cells derived from even those tissues which are generally difficult to culture, such as brain or peripheral tissue cells. Furthermore, by using such cells, drugs which activate the functions of various tissues may be selected. Moreover, if a high-expression cell line is provided, it will be possible to isolate and purify the protein of the present invention from the cell line.

In the specification and drawings of the present application, the abbreviations used for bases (nucleotides), amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate dCTP: Deoxycytidine triphosphate
ATP: Adenosine triphosphate
EDTA: Ethylenediaminetetracetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
pGlu: Pyroglutamic acid
Me: Methyl
Et: Ethyl
Bu: Butyl
Ph: Phenyl
TC: Thiazolidine-4(R)-carboxamide Substitution groups, protecting groups and reagents used in the specification of the present application are represented by the symbols set forth below.

Tos: p-toluene sulfonyl
CHO: Formyl
Bzl: Benzyl
Cl$_2$Bzl: 2,6-dichlorobenzyl
Bom: Benzyloxymethyl
Z: Benzyloxycarbonyl
Cl-Z: 2-chlorobenzyloxycarbonyl
Br-Z: 2-bromobenzyloxycarbonyl
Boc: Tert-butoxycarbonyl
DNP: Dinitrophenol
Trt: Trityl
Bum: Tert-butoxymethyl
Fmoc: N-9-fluorenylmethyloxycarbonyl
HOBt: 1-hydroxybenzotriazole
HOOBt: 3,4-dihydro-3-hydroxy-4-oxo-1,2,3-benzotriazine
HONB: 1-hydroxy-5-norbornene-2,3-dicarboximide
DCC: Dicyclohexylcarbodiimide Each SEQ ID NO set forth in the SEQUENCE LISTING of the specification refers to the following sequence:

SEQ ID NO:1 shows an amino acid sequence of the human leukocyte-derived protein of the present invention.

SEQ ID NO:2 shows an amino acid sequence of the human leukocyte-derived protein of the present invention (FIG. 1), wherein 9 amino acid residues are added to the N-terminus of the amino acid sequence represented by SEQ ID NO:1.

SEQ ID NO:3 shows an amino acid sequence of the partial peptide of the human leukocyte-derived protein of the present invention.

SEQ ID NO:4 shows an amino acid sequence of the partial peptide of the human leukocyte-derived protein of the present invention.

SEQ ID NO:5 shows a nucleotide sequence of the DNA coding for the human leukocyte-derived protein represented by SEQ ID NO:1 of the present invention.

SEQ ID NO:6 shows a nucleotide sequence of the DNA coding for the human leukocyte-derived protein represented by SEQ ID NO:2 of the present invention.

SEQ ID NO:7 shows a nucleotide sequence of the DNA coding for the partial peptide represented by SEQ ID NO:3 of the human leukocyte-derived protein of the present invention.

SEQ ID NO:8 shows a nucleotide sequence of the DNA coding for the partial peptide represented by SEQ ID NO:4 of the human leukocyte-derived protein of the present invention.

SEQ ID NO:9 shows an amino acid sequence of the human calpain small subunit.

SEQ ID NO:10 shows a nucleotide sequence of the DNA coding for human calpain small subunit.

SEQ ID NO:11 shows a nucleotide sequence of the synthetic primer used for the cloning of the DNA coding for the protein of the present invention in Example 1.

SEQ ID NO:12 shows a nucleotide sequence of the synthetic primer used for the cloning of the DNA coding for the protein of the present invention in Example 1.

SEQ ID NO:13 shows a nucleotide sequence of the synthetic primer used for the cloning of the DNA coding for the protein of the present invention in Example 1.

SEQ ID NO:14 shows a nucleotide sequence of the fragment of the DNA coding for the protein of the present invention used for the northern blot analysis of Example 2.

SEQ ID NO:15 shows a nucleotide sequence of the fragment of the DNA coding for human $\mu$-calpain large subunit used for the northern blot analysis of Example 2.

SEQ ID NO:16 shows a nucleotide sequence of the fragment of the DNA coding for human calpain small subunit used for the northern blot analysis of Example 2.

SEQ ID NO:17 shows a nucleotide sequence of the synthetic primer used for the construction of the DNA coding for the protein of the present invention in Example 3.

SEQ ID NO:18 shows a nucleotide sequence of the synthetic primer used for the construction of the DNA coding for the protein of the present invention in Example 3.

The transformant strain of *Escherichia coli*, designated DH10B/PTB1915, which is obtained in the Example 1 mentioned hereinafter, is on deposit under the terms of the Budapest Treaty from Apr. 2, 1996, with NIBH and has been assigned the Accession Number FERM BP-5496. It is also on deposit from Apr. 3, 1996 with IFO and has been assigned the Accession Number IFO 15935.

EXAMPLES

The following reference examples and examples are intended to illustrate the present invention in further detail and should by no means be construed as defining the scope of the invention. Incidentally, the gene manipulations using *Escherichia coli* were made according to the protocol described in Molecular Cloning.

Example 1

Cloning of a Gene Coding for a Human Calpain

The cloning of the cDNA was carried out using Gene GENETRAPPER™ cDNA Positive Selection System (GIBCO/BRL).

*Escherichia coli* DH12S cells from a human leukocyte-derived cDNA library (GIBCO/BRL) were cultured in Terrific Broth (12 g/l bacto-tryptone (Difco), 24 g/l bacto-yeast extract (Difco), 2.3 g/l potassium dihydrogen phosphate, 12.5 g/l potassium monohydrogen phosphate) at 30° C. for 16 hours and the amplified plasmid cDNA library was purified and extracted by using QIAGEN Plasmid Kit (QIAGEN). The purified plasmid cDNA library was then digested with Gene II and Exo III (both from GIBCO/BRL) to prepare the single-stranded cDNA library.

On the other hand, a synthetic oligonucleotide (SEQ ID NO:11) was used as a probe for screening for the cDNA. The probe was labeled by biotinylating its 3'-end with TdT and biotin-14-dCTP (GIBCO/BRL). The single-stranded cDNA library was treated at 95° C. for 1 minute, and then immediately incubated on ice. The biotinylated probe was added, and hybridized to the library DNA solution at 37° C. for one hour. After hybridization, magnet beads in GENETRAPPER™ cDNA Positive Selection System were added to the solution and the mixture was allowed to stand at room temperature for 30 minutes with stirring at 2-min intervals. Thereafter, the mixture was allowed to sit in a magnet rack in GENETRAPPER™ cDNA Positive Selection System for 2 minutes. The supernatant was then discarded and the magnet beads were washed three times with wash buffer in GENETRAPPER™ cDNA Positive Selection System. DNA was then eluted from the magnetic beads with elution buffer in GENETRAPPER™ cDNA Positive Selection System.

The synthetic oligonucleotide (SEQ ID NO:11) as a primer was mixed with the DNA solution thus obtained, and the mixture was incubated at 95° C. for 1 minute. Then, by adding repair enzyme in GENETRAPPER™ cDNA Positive Selection System to the solution, double-stranded DNA was synthesized at 70° C. for 15 minutes. Using an electroporation apparatus (Bio-Rad), the synthesized dsDNA was introduced into *Escherichia coli* DH10B cells.

Screening for desired cDNA clones among the obtained transformants was carried out by colony PCR using two oligonucleotides (SEQ ID NO:12 and NO:13) as primers. Two colonies, from which a 712 bp DNA fragment was amplified, were selected as positive clones.

The selected *Escherichia coli* clones were cultured individually and the plasmid DNAs were recovered. After the reaction using Taq dideoxy terminator cycle sequencing kit (Perkin-Elmer), the cDNA inserts of the plasmids were sequenced with a 373A DNA Sequencer (Perkin-Elmer). The two obtained clones coded for the same gene and had a 2970-base sequence containing a polyadenylation signal (FIG. 1). Encoded in this cDNA fragment was a novel calpain composed of 703 amino acid residues as represented by SEQ ID NO:1 or 712 amino acid residues as represented by SEQ ID NO:2. The active site residues, cysteine, histidine, and asparagine (the 105th, 262nd, and 286th amino acid residues of the amino acid sequence represented by SEQ ID NO:1), were also found to be conserved (FIG. 1). Moreover, whereas it showed the highest homology with rat nCL-2, the identity at amino acid level was only 84%.

The plasmid pTB1915 containing the DNA encoding the protein of the present invention was introduced into *Escherichia coli* DH10B to obtain a transformant *Escherichia coli* DH10B/pTB1915.

Example 2

Northern Blot Analysis on Tissue Distribution of Gene Expression of the Calpain Gene Northern blot analysis on tissue distribution of gene expression of the calpain gene was carried out by using Human Multiple Tissue Northern Blot (Clontech) and Human Multiple Tissue Northern Blot II (Clontech) membrane filters. The membrane filters were subjected to 3 hours of prehybridization at 50° C. in hybridization buffer (50% deionized formamide, 5×SSPE, 2×Denhardt's solution, 2% SDS, 100 μg/ml heat-denaturated herring sperm DNA). On the other hand, the DNA fragment encoding the protein of the invention as represented by SEQ ID NO:14 was used as a probe and labeled using ($\alpha$-$^{32}$P)dCTP (Amersham) and Bca Best Labeling Kit (Takara Shuzo). The hybridization was carried out in the labeled probe-containing hybridization buffer (50% deionized formamide, 5×SSPE, 2×Denhardt's solution, 2% SDS, 100 μg/ml heat-denaturated herring sperm DNA) at 50° C. for 18 hours.

The filters were washed twice with 2×SSC/0.05% SDS solution at room temperature and further washed twice in 0.1×SSC/0.1% SDS at 50° C. Autoradiography was carried out to detect the RNAs hybridized to the probe. As a result, the bands were detected in lung and large intestine and both RNAs were about 3.0 kb×long. The above filters were then treated in boiling 0.5% SDS for 10 minutes to be reprobed. Then, using the DNA fragment of SEQ ID NO:15 as a probe for human μ-calpain large subunit, the DNA fragment of SEQ ID NO:16 as a probe for human calpain small subunit, and the human β-actin control probe (Clontech) as the probe for β-actin, hybridization reactions were carried out under the same conditions as above. As a result, bands of about 3.0 kb were found in all tissues for human μ-calpain large subunit and bands of about 1.5 kb and about 5.0 kb were found in all tissues for human calpain small subunit (FIG. 3).

Example 3

Expression of the Recombinant Calpain in *Escherichia coli*

An expression plasmid, pGST/calpain, is derived from a vector pGEX-4T-3(Pharmacia Biotech) containing:

1) *Escherichia coli* replication origin, 2) ampicillin resistance gene, 3) tac promoter followed by glutathione S-transferase (GST) gene, a thrombin cleavage site and a multicloning site (MCS). A DNA fragment encoding the entire calpain is cloned into the MCS of the vector. Therefore, the recombinant protein is fused in frame to GST to its 5' end and its expression is directed under the tac promoter. By the GST epitope fused in the protein, the recombinant protein is easily detected by an antibody that recognizes the GST epitope and purified by an affinity matrix Glutathione Sepharose 4B.

The plasmid construction strategy is described as follows: The DNA sequence coding for the calpain of the present invention is constructed by PCR on the full-length calpain by using two primers: the 5' primer 5'-ATGGGATCCAAGCAAGAGCCCACGGCCA-3' (SEQ ID NO:17), which contains a restriction site of BamHI followed by 16 nucleotides of the calpain coding sequence starting from downstream of the initiation codon; the 3' primer 5'-TGACTGCAGAAACCCCCGGGTCAGAC-3' (SEQ ID NO:18), which contains a restriction site of PstI and the last 6 nucleotides of the calpain coding sequence including the stop codon. A PCR amplified DNA fragment is subcloned into a plasmid, pBluescript$^R$II (STRATAGENE) by BamHI/PstI end ligation. After digestion of the plasmid with both BamHI and PstI, a DNA fragment containing calpain coding sequence is recovered and ligated with pGEX-4T-3 by BamHI/PstI end ligation. The resultant plasmid DNA is isolated from transformants and examined by sequence analysis for the presence of the correct fragment. For expression of the recombinant calpain, *Escherichia coli* JM109 carrying the expression vector is cultured in the presence of 1.0 mM isopropyl-β-thiogalactoside (IPTG). The expression of the recombinant calpain can be detected by GST Detection Kit containing an antibody that recognizes the GST epitope (Pharmacia Biotech). Glutathione Sepharose 4B or Prepacked Glutathione Sepharose 4B columns can also be used for purification of the recombinant protein from cell extracts.

Example 4

Expression of the Recombinant Calpain in COS Cells

The pTB1915 obtained in Example 1, which is derived from an expression vector plasmid, pCMV·SPORT(GIBCO/BRL), is used for expression in animal cells. This vector is a pUC-derived plasmid and contains a CMV promoter followed by a multicloning site and a SV40 polyadenylation site. The COS-7 cells (purchased from Institute for Fermentation, Osaka) are cultured in DMEM containing 10% fetal bovine serum (FBS) until they are grown 50% confluently. Then the cells are transfected with the pTB1915 by using TRANSFECTAM (Nippon Gene). After incubation of the cells with the DNA in the absence of FBS under 5% $CO_2$ at 37° C. for 4 hours, FBS is added (final 10%) to the cells and they are further incubated for 20 hours followed by medium exchange with serum-free DMEM. Three days later, the culture media are then collected and the cell extracts are prepared by lysing with with RIPA buffer (150 mM NaCl, 1% NP-40, 0.1% SDS, 0.5% DOC, 40 mM Tris, pH 7.5).

What is claimed is:

1. An isolated DNA which contains a DNA comprising a nucleotide sequence coding for a protein comprising the amino acid sequence represented by SEQ ID NO:1 or SEQ ID NO:2 or a salt thereof.

2. The DNA according to claim 1, which comprises a nucleotide sequence represented by SEQ ID NO:5 or SEQ ID NO.6.

3. A recombinant vector comprising the DNA according to claim 1.

4. A transformant carrying the recombinant vector according to claim 3.

5. A process for producing a protein or a salt thereof comprising the amino acid sequence represented by SEQ ID NO:1 or SEQ ID NO:2, which comprises culturing a transformant according to claim 4 under conditions suitable to express said protein.

* * * * *

```
                        SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
        (A) LENGTH: 703 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

Met Ala Ala Gln Ala Ala Gly Val Ser Arg Gln Arg Ala Ala Thr Gln
1               5                  10                  15

Gly Leu Gly Ser Asn Gln Asn Ala Leu Lys Tyr Leu Gly Gln Asp Phe
                20                  25                  30

Lys Thr Leu Arg Gln Gln Cys Leu Asp Ser Gly Val Leu Phe Lys Asp
            35                  40                  45

Pro Glu Phe Pro Ala Cys Pro Ser Ala Leu Gly Tyr Lys Asp Leu Gly
    50                  55                  60

Pro Gly Ser Pro Gln Thr Gln Gly Ile Ile Trp Lys Arg Pro Thr Glu
65                  70                  75                  80

Leu Cys Pro Ser Pro Gln Phe Ile Val Gly Gly Ala Thr Arg Thr Asp
                85                  90                  95

Ile Cys Gln Gly Gly Leu Gly Asp Cys Trp Leu Leu Ala Ala Ile Ala
                100                 105                 110

Ser Leu Thr Leu Asn Glu Glu Leu Leu Tyr Arg Val Val Pro Arg Asp
            115                 120                 125

Gln Asp Phe Gln Glu Asn Tyr Ala Gly Ile Phe His Phe Gln Phe Trp
    130                 135                 140

Gln Tyr Gly Glu Trp Val Glu Val Val Ile Asp Asp Arg Leu Pro Thr
145                 150                 155                 160

Lys Asn Gly Gln Leu Leu Phe Leu His Ser Glu Gln Gly Asn Glu Phe
                165                 170                 175

Trp Ser Ala Leu Leu Glu Lys Ala Tyr Ala Lys Leu Asn Gly Cys Tyr
            180                 185                 190

Glu Ala Leu Ala Gly Gly Ser Thr Val Glu Gly Phe Glu Asp Phe Thr
        195                 200                 205
```

-continued

```
Gly Gly Ile Ser Glu Phe Tyr Asp Leu Lys Lys Pro Ala Asn Leu
    210                 215                 220

Tyr Gln Ile Ile Arg Lys Ala Leu Cys Ala Gly Ser Leu Leu Gly Cys
225                 230                 235                 240

Ser Ile Asp Val Ser Ser Ala Ala Glu Ala Glu Ala Ile Thr Ser Gln
                    245                 250                 255

Lys Leu Val Lys Ser His Ala Tyr Ser Val Thr Gly Val Glu Glu Val
            260                 265                 270

Asn Phe Gln Gly His Pro Glu Lys Leu Ile Arg Leu Arg Asn Pro Trp
        275                 280                 285

Gly Glu Val Glu Trp Ser Gly Ala Trp Ser Asp Asp Ala Pro Glu Trp
    290                 295                 300

Asn His Ile Asp Pro Arg Arg Lys Glu Glu Leu Asp Lys Lys Val Glu
305                 310                 315                 320

Asp Gly Glu Phe Trp Met Ser Leu Ser Asp Phe Val Arg Gln Phe Ser
                325                 330                 335

Arg Leu Glu Ile Cys Asn Leu Ser Pro Asp Ser Leu Ser Ser Glu Glu
            340                 345                 350

Val His Lys Trp Asn Leu Val Leu Phe Asn Gly His Trp Thr Arg Gly
        355                 360                 365

Ser Thr Ala Gly Gly Cys Gln Asn Tyr Pro Ala Thr Tyr Trp Thr Asn
    370                 375                 380

Pro Gln Phe Lys Ile Arg Leu Asp Glu Val Asp Glu Asp Gln Glu Glu
385                 390                 395                 400

Ser Ile Gly Glu Pro Cys Cys Thr Val Leu Leu Gly Leu Met Gln Lys
                405                 410                 415

Asn Arg Arg Trp Arg Lys Arg Ile Gly Gln Gly Met Leu Ser Ile Gly
            420                 425                 430

Tyr Ala Val Tyr Gln Val Pro Lys Glu Leu Glu Ser His Thr Asp Ala
        435                 440                 445

His Leu Gly Arg Asp Phe Phe Leu Ala Tyr Gln Pro Ser Ala Arg Thr
    450                 455                 460

Ser Thr Tyr Val Asn Leu Arg Glu Val Ser Gly Arg Ala Arg Leu Pro
465                 470                 475                 480

Pro Gly Glu Tyr Leu Val Val Pro Ser Thr Phe Glu Pro Phe Lys Asp
                485                 490                 495

Gly Glu Phe Cys Leu Arg Val Phe Ser Glu Lys Lys Ala Gln Ala Leu
            500                 505                 510

Glu Ile Gly Asp Val Val Ala Gly Asn Pro Tyr Glu Pro His Pro Ser
        515                 520                 525

Glu Val Asp Gln Glu Asp Asp Gln Phe Arg Arg Leu Phe Glu Lys Leu
    530                 535                 540

Ala Gly Lys Asp Ser Glu Ile Thr Ala Asn Ala Leu Lys Ile Leu Leu
545                 550                 555                 560

Asn Glu Ala Phe Ser Lys Arg Thr Asp Ile Lys Phe Asp Gly Phe Asn
                565                 570                 575

Ile Asn Thr Cys Arg Glu Met Ile Ser Leu Leu Asp Ser Asn Gly Thr
            580                 585                 590

Gly Thr Leu Gly Ala Val Glu Phe Lys Thr Leu Trp Leu Lys Ile Gln
        595                 600                 605

Lys Tyr Leu Glu Ile Tyr Trp Glu Thr Asp Tyr Asn His Ser Gly Thr
    610                 615                 620
```

```
Ile Asp Ala His Glu Met Arg Thr Ala Leu Arg Lys Ala Gly Phe Thr
625                 630                 635                 640

Leu Asn Ser Gln Val Gln Gln Thr Ile Ala Leu Arg Tyr Ala Cys Ser
            645                 650                 655

Lys Leu Gly Ile Asn Phe Asp Ser Phe Val Ala Cys Met Ile Arg Leu
                660                 665                 670

Glu Thr Leu Phe Lys Leu Phe Ser Leu Leu Asp Glu Asp Lys Asp Gly
        675                 680                 685

Met Val Gln Leu Ser Leu Ala Glu Trp Leu Cys Cys Val Leu Val
        690                 695                 700
```

(2) INFORMATION FOR SEQ ID NO:2:

(i) SEQUENCE CHARACTERISTICS:
        (A) LENGTH: 712 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Gly Leu Lys Gln Glu Pro Thr Ala Met Ala Ala Gln Ala Ala Gly
1               5                   10                  15

Val Ser Arg Gln Arg Ala Ala Thr Gln Gly Leu Gly Ser Asn Gln Asn
            20                  25                  30

Ala Leu Lys Tyr Leu Gly Gln Asp Phe Lys Thr Leu Arg Gln Gln Cys
        35                  40                  45

Leu Asp Ser Gly Val Leu Phe Lys Asp Pro Glu Phe Pro Ala Cys Pro
50                  55                  60

Ser Ala Leu Gly Tyr Lys Asp Leu Gly Pro Gly Ser Pro Gln Thr Gln
65                  70                  75                  80

Gly Ile Ile Trp Lys Arg Pro Thr Glu Leu Cys Pro Ser Pro Gln Phe
                85                  90                  95

Ile Val Gly Gly Ala Thr Arg Thr Asp Ile Cys Gln Gly Gly Leu Gly
                100                 105                 110

Asp Cys Trp Leu Leu Ala Ala Ile Ala Ser Leu Thr Leu Asn Glu Glu
            115                 120                 125

Leu Leu Tyr Arg Val Val Pro Arg Asp Gln Asp Phe Gln Glu Asn Tyr
130                 135                 140

Ala Gly Ile Phe His Phe Gln Phe Trp Gln Tyr Gly Glu Trp Val Glu
145                 150                 155                 160

Val Val Ile Asp Asp Arg Leu Pro Thr Lys Asn Gly Gln Leu Leu Phe
                165                 170                 175

Leu His Ser Glu Gln Gly Asn Glu Phe Trp Ser Ala Leu Leu Glu Lys
            180                 185                 190

Ala Tyr Ala Lys Leu Asn Gly Cys Tyr Glu Ala Leu Ala Gly Gly Ser
        195                 200                 205

Thr Val Glu Gly Phe Glu Asp Phe Thr Gly Gly Ile Ser Glu Phe Tyr
        210                 215                 220

Asp Leu Lys Lys Pro Pro Ala Asn Leu Tyr Gln Ile Ile Arg Lys Ala
225                 230                 235                 240

Leu Cys Ala Gly Ser Leu Leu Gly Cys Ser Ile Asp Val Ser Ser Ala
                245                 250                 255

Ala Glu Ala Glu Ala Ile Thr Ser Gln Lys Leu Val Lys Ser His Ala
                260                 265                 270
```

-continued

```
Tyr Ser Val Thr Gly Val Glu Val Asn Phe Gln Gly His Pro Glu
        275                 280                 285

Lys Leu Ile Arg Leu Arg Asn Pro Trp Gly Glu Val Glu Trp Ser Gly
        290                 295                 300

Ala Trp Ser Asp Asp Ala Pro Glu Trp Asn His Ile Asp Pro Arg Arg
305                 310                 315                 320

Lys Glu Glu Leu Asp Lys Lys Val Glu Asp Gly Glu Phe Trp Met Ser
                325                 330                 335

Leu Ser Asp Phe Val Arg Gln Phe Ser Arg Leu Glu Ile Cys Asn Leu
                340                 345                 350

Ser Pro Asp Ser Leu Ser Ser Glu Glu Val His Lys Trp Asn Leu Val
                355                 360                 365

Leu Phe Asn Gly His Trp Thr Arg Gly Ser Thr Ala Gly Gly Cys Gln
        370                 375                 380

Asn Tyr Pro Ala Thr Tyr Trp Thr Asn Pro Gln Phe Lys Ile Arg Leu
385                 390                 395                 400

Asp Glu Val Asp Glu Asp Gln Glu Glu Ser Ile Gly Glu Pro Cys Cys
                405                 410                 415

Thr Val Leu Leu Gly Leu Met Gln Lys Asn Arg Arg Trp Arg Lys Arg
                420                 425                 430

Ile Gly Gln Gly Met Leu Ser Ile Gly Tyr Ala Val Tyr Gln Val Pro
        435                 440                 445

Lys Glu Leu Glu Ser His Thr Asp Ala His Leu Gly Arg Asp Phe Phe
        450                 455                 460

Leu Ala Tyr Gln Pro Ser Ala Arg Thr Ser Thr Tyr Val Asn Leu Arg
465                 470                 475                 480

Glu Val Ser Gly Arg Ala Arg Leu Pro Pro Gly Glu Tyr Leu Val Val
                485                 490                 495

Pro Ser Thr Phe Glu Pro Phe Lys Asp Gly Glu Phe Cys Leu Arg Val
            500                 505                 510

Phe Ser Glu Lys Lys Ala Gln Ala Leu Glu Ile Gly Asp Val Val Ala
            515                 520                 525

Gly Asn Pro Tyr Glu Pro His Pro Ser Glu Val Asp Gln Glu Asp Asp
        530                 535                 540

Gln Phe Arg Arg Leu Phe Glu Lys Leu Ala Gly Lys Asp Ser Glu Ile
545                 550                 555                 560

Thr Ala Asn Ala Leu Lys Ile Leu Leu Asn Glu Ala Phe Ser Lys Arg
                565                 570                 575

Thr Asp Ile Lys Phe Asp Gly Phe Asn Ile Asn Thr Cys Arg Glu Met
                580                 585                 590

Ile Ser Leu Leu Asp Ser Asn Gly Thr Gly Thr Leu Gly Ala Val Glu
        595                 600                 605

Phe Lys Thr Leu Trp Leu Lys Ile Gln Lys Tyr Leu Glu Ile Tyr Trp
        610                 615                 620

Glu Thr Asp Tyr Asn His Ser Gly Thr Ile Asp Ala His Glu Met Arg
625                 630                 635                 640

Thr Ala Leu Arg Lys Ala Gly Phe Thr Leu Asn Ser Gln Val Gln Gln
                645                 650                 655

Thr Ile Ala Leu Arg Tyr Ala Cys Ser Lys Leu Gly Ile Asn Phe Asp
                660                 665                 670

Ser Phe Val Ala Cys Met Ile Arg Leu Glu Thr Leu Phe Lys Leu Phe
                675                 680                 685
```

```
Ser Leu Leu Asp Glu Asp Lys Asp Gly Met Val Gln Leu Ser Leu Ala
    690                 695                 700

Glu Trp Leu Cys Cys Val Leu Val
705                 710

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Cys Gln Gly Gly Leu Gly Asp Cys
1               5

(2) INFORMATION FOR SEQ ID NO:4:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

His Ala Tyr Ser Val Thr Gly Val Glu Glu Val Asn Phe Gln Gly His
1               5                   10                  15

Pro Glu Lys Leu Ile Arg Leu Arg Asn
            20                  25

(2) INFORMATION FOR SEQ ID NO:5:

(i) SEQUENCE CHARACTERISTICS:
        (A) LENGTH: 2109 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

ATGGCAGCCC AGGCAGCTGG TGTATCTAGG CAGCGGGCAG CCACTCAAGG TCTTGGCTCC      60

AACCAAAACG CTTTGAAGTA CTTGGGCCAG GATTTCAAGA CCCTGAGGCA ACAGTGCTTG     120

GACTCAGGGG TCCTATTTAA GGACCCTGAG TTCCCAGCAT GTCCATCAGC TTTGGGCTAC     180

AAGGATCTTG ACCAGGCTC TCCGCAAACT CAAGGCATCA TCTGGAAGCG GCCCACGGAG      240

TTGTGTCCCA GCCCTCAGTT TATCGTTGGT GGAGCCACGC GCACAGACAT TTGTCAGGGT     300

GGTCTAGGTG ACTGCTGGCT TCTGGCTGCC ATTGCCTCCC TGACCCTGAA TGAAGAGCTG     360

CTTTACCGGG TGGTCCCCAG GGACCAGGAC TTCCAGGAGA ACTATGCGGG AATCTTTCAC     420

TTTCAGTTCT GGCAGTACGG AGAGTGGGTG GAGGTGGTCA TTGACGACAG GCTGCCCACC     480

AAGAATGGAC AGCTGCTCTT CCTACACTCG GAACAAGGCA ATGAATTCTG GAGTGCCCTG     540

CTGGAGAAAG CCTATGCCAA GCTTAATGGT TGTTATGAGG CTCTCGCTGG AGGTTCCACA     600

GTGGAGGGGT TGAGGATTT CACAGGTGGC ATCTCTGAGT TTTATGACCT GAAGAAACCA     660

CCAGCCAATC TATATCAGAT CATCCGGAAG GCCCTCTGTG CGGGGTCTCT GCTGGGCTGC     720
```

```
TCCATTGATG TCTCCAGTGC AGCCGAAGCC GAAGCCATCA CCAGCCAGAA GCTGGTTAAG      780

AGTCATGCGT ACTCTGTCAC TGGAGTCGAA GAGGTGAATT TCCAGGGCCA TCCAGAGAAG      840

CTGATCAGAC TCAGGAATCC ATGGGGTGAA GTGGAGTGGT CGGAGCCTG GAGCGATGAT       900

GCACCAGAGT GGAATCACAT AGACCCCCGG CGGAAGGAAG AACTGGACAA GAAAGTTGAG      960

GATGGAGAAT TCTGGATGTC ACTTTCAGAT TTCGTGAGGC AGTTCTCTCG GTTGGAGATC     1020

TGCAACCTGT CCCCGGACTC TCTGAGTAGC GAGGAGGTGC ACAAATGGAA CCTGGTCCTG    1080

TTCAACGGCC ACTGGACCCG GGGCTCCACA GCTGGGGGCT GCCAGAACTA CCCAGCCACG   1140

TACTGGACCA ATCCCCAGTT CAAAATCCGT TTGGATGAAG TGGATGAGGA CCAGGAGGAG   1200

AGCATCGGTG AACCCTGCTG TACAGTGCTG CTGGGCCTGA TGCAGAAAAA TCGCAGGTGG   1260

CGGAAGCGGA TAGGACAAGG CATGCTTAGC ATCGGCTATG CCGTCTACCA GGTTCCCAAG   1320

GAGCTGGAGA GTCACACGGA CGCACACTTG GGCCGGGATT TCTTCCTGGC CTACCAGCCC   1380

TCAGCCCGCA CCAGCACCTA CGTCAACCTG CGGGAGGTCT CTGGCCGGGC CCGGCTGCCC   1440

CCTGGGGAGT ACCTGGTGGT GCCATCCACA TTTGAACCCT TCAAAGACGG CGAGTTCTGC   1500

TTGAGAGTGT TCTCAGAGAA GAAGGCCCAG GCCCTAGAAA TTGGGGATGT GGTAGCTGGA   1560

AACCCATATG AGCCACATCC CAGTGAGGTG GATCAGGAAG ATGACCAGTT CAGGAGGCTG   1620

TTTGAGAAGT TGGCAGGGAA GGATTCTGAG ATTACTGCCA ATGCACTCAA GATACTTTTG   1680

AATGAGGCGT TTTCCAAGAG AACAGACATA AAATTCGATG GATTCAACAT CAACACTTGC   1740

AGGGAAATGA TCAGTCTGTT GGATAGCAAT GGAACGGGCA CTTTGGGGGC GGTGGAATTC   1800

AAGACGCTCT GGCTGAAGAT TCAGAAGTAT CTGGAGATCT ATTGGGAAAC TGATTATAAC   1860

CACTCGGGCA CCATCGATGC CCACGAGATG AGGACAGCCC TCAGGAAGGC AGGTTTCACC   1920

CTCAACAGCC AGGTGCAGCA GACCATTGCC CTGCGGTATG CGTGCAGCAA GCTCGGCATC   1980

AACTTTGACA GCTTCGTGGC TTGTATGATC CGCCTGGAGA CCCTCTTCAA ACTATTCAGC   2040

CTTCTGGACG AAGACAAGGA TGGCATGGTT CAGCTCTCTC TGGCCGAGTG GCTGTGCTGC   2100

GTGTTGGTC                                                                                                                     2109

(2) INFORMATION FOR SEQ ID NO:6:

(i) SEQUENCE CHARACTERISTICS:
        (A) LENGTH: 2136 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

ATGGGCTTGA AGCAAGAGCC CACGGCCATG GCAGCCCAGG CAGCTGGTGT ATCTAGGCAG       60

CGGGCAGCCA CTCAAGGTCT TGGCTCCAAC CAAAACGCTT TGAAGTACTT GGGCCAGGAT      120

TTCAAGACCC TGAGGCAACA GTGCTTGGAC TCAGGGGTCC TATTTAAGGA CCCTGAGTTC      180

CCAGCATGTC CATCAGCTTT GGGCTACAAG GATCTTGGAC CAGGCTCTCC GCAAACTCAA      240

GGCATCATCT GGAAGCGGCC CACGGAGTTG TGTCCCAGCC CTCAGTTTAT CGTTGGTGGA      300

GCCACGCGCA CAGACATTTG TCAGGGTGGT CTAGGTGACT GCTGGCTTCT GGCTGCCATT      360

GCCTCCCTGA CCCTGAATGA AGAGCTGCTT TACCGGGTGG TCCCCAGGGA CCAGGACTTC      420

CAGGAGAACT ATGCGGGAAT CTTTCACTTT CAGTTCTGGC AGTACGGAGA GTGGGTGGAG      480

GTGGTCATTG ACGACAGGCT GCCCACCAAG AATGGACAGC TGCTCTTCCT ACACTCGGAA      540
```

| | |
|---|---|
| CAAGGCAATG AATTCTGGAG TGCCCTGCTG GAGAAAGCCT ATGCCAAGCT TAATGGTTGT | 600 |
| TATGAGGCTC TCGCTGGAGG TTCCACAGTG GAGGGGTTTG AGGATTTCAC AGGTGGCATC | 660 |
| TCTGAGTTTT ATGACCTGAA GAAACCACCA GCCAATCTAT ATCAGATCAT CCGGAAGGCC | 720 |
| CTCTGTGCGG GGTCTCTGCT GGGCTGCTCC ATTGATGTCT CCAGTGCAGC CGAAGCCGAA | 780 |
| GCCATCACCA GCCAGAAGCT GGTTAAGAGT CATGCGTACT CTGTCACTGG AGTCGAAGAG | 840 |
| GTGAATTTCC AGGGCCATCC AGAGAAGCTG ATCAGACTCA GGAATCCATG GGGTGAAGTG | 900 |
| GAGTGGTCGG GAGCCTGGAG CGATGATGCA CCAGAGTGGA ATCACATAGA CCCCCGGCGG | 960 |
| AAGGAAGAAC TGGACAAGAA AGTTGAGGAT GGAGAATTCT GGATGTCACT TTCAGATTTC | 1020 |
| GTGAGGCAGT TCTCTCGGTT GGAGATCTGC AACCTGTCCC CGGACTCTCT GAGTAGCGAG | 1080 |
| GAGGTGCACA AATGGAACCT GGTCCTGTTC AACGGCCACT GGACCCGGGG CTCCACAGCT | 1140 |
| GGGGGCTGCC AGAACTACCC AGCCACGTAC TGGACCAATC CCCAGTTCAA AATCCGTTTG | 1200 |
| GATGAAGTGG ATGAGGACCA GGAGGAGAGC ATCGGTGAAC CCTGCTGTAC AGTGCTGCTG | 1260 |
| GGCCTGATGC AGAAAAATCG CAGGTGGCGG AAGCGGATAG GACAAGGCAT GCTTAGCATC | 1320 |
| GGCTATGCCG TCTACCAGGT TCCCAAGGAG CTGGAGAGTC ACACGGACGC ACACTTGGGC | 1380 |
| CGGGATTTCT TCCTGGCCTA CCAGCCCTCA GCCCGCACCA GCACCTACGT CAACCTGCGG | 1440 |
| GAGGTCTCTG GCCGGGCCCG GCTGCCCCCT GGGGAGTACC TGGTGGTGCC ATCCACATTT | 1500 |
| GAACCCTTCA AGACGGCGA GTTCTGCTTG AGAGTGTTCT CAGAGAAGAA GGCCCAGGCC | 1560 |
| CTAGAAATTG GGGATGTGGT AGCTGGAAAC CCATATGAGC CACATCCCAG TGAGGTGGAT | 1620 |
| CAGGAAGATG ACCAGTTCAG GAGGCTGTTT GAGAAGTTGG CAGGGAAGGA TTCTGAGATT | 1680 |
| ACTGCCAATG CACTCAAGAT ACTTTTGAAT GAGGCGTTTT CCAAGAGAAC AGACATAAAA | 1740 |
| TTCGATGGAT TCAACATCAA CACTTGCAGG GAAATGATCA GTCTGTTGGA TAGCAATGGA | 1800 |
| ACGGGCACTT TGGGGGCGGT GGAATTCAAG ACGCTCTGGC TGAAGATTCA GAAGTATCTG | 1860 |
| GAGATCTATT GGGAAACTGA TTATAACCAC TCGGGCACCA TCGATGCCCA CGAGATGAGG | 1920 |
| ACAGCCCTCA GGAAGGCAGG TTTCACCCTC AACAGCCAGG TGCAGCAGAC CATTGCCCTG | 1980 |
| CGGTATGCGT GCAGCAAGCT CGGCATCAAC TTTGACAGCT TCGTGGCTTG TATGATCCGC | 2040 |
| CTGGAGACCC TCTTCAAACT ATTCAGCCTT CTGGACGAAG ACAAGGATGG CATGGTTCAG | 2100 |
| CTCTCTCTGG CCGAGTGGCT GTGCTGCGTG TTGGTC | 2136 |

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

| | |
|---|---|
| TGTCAGGGTG GTCTAGGTGA CTGC | 24 |

(2) INFORMATION FOR SEQ ID NO:8:

(i) SEQUENCE CHARACTERISTICS:
        (A) LENGTH: 75 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

CATGCGTACT CTGTCACTGG AGTCGAAGAG GTGAATTTCC AGGGCCATCC AGAGAAGCTG      60

ATCAGACTCA GGAAT      75

(2) INFORMATION FOR SEQ ID NO:9:

(i) SEQUENCE CHARACTERISTICS:
         (A) LENGTH: 268 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:9:

Met Phe Leu Val Asn Ser Phe Leu Lys Gly Gly Gly Gly Gly Gly
  1               5                  10                  15

Gly Gly Gly Gly Leu Gly Gly Gly Leu Gly Asn Val Leu Gly Gly Leu
                20                  25                  30

Ile Ser Gly Ala Gly Gly Gly Gly Gly Gly Gly Gly Gly Gly Gly
     35                  40                  45

Gly Gly Gly Gly Gly Gly Gly Thr Ala Met Arg Ile Leu Gly Gly
 50                  55                  60

Val Ile Ser Ala Ile Ser Glu Ala Ala Ala Gln Tyr Asn Pro Glu Pro
 65                  70                  75                  80

Pro Pro Pro Arg Thr His Tyr Ser Asn Ile Glu Ala Asn Glu Ser Glu
                85                  90                  95

Glu Val Arg Gln Phe Arg Arg Leu Phe Ala Gln Leu Ala Gly Asp Asp
                100                 105                 110

Met Glu Val Ser Ala Thr Glu Leu Met Asn Ile Leu Asn Lys Val Val
                115                 120                 125

Thr Arg His Pro Asp Leu Lys Thr Asp Gly Phe Gly Ile Asp Thr Cys
 130                 135                 140

Arg Ser Met Val Ala Val Met Asp Ser Asp Thr Thr Gly Lys Leu Gly
 145                 150                 155                 160

Phe Glu Glu Phe Lys Tyr Leu Trp Asn Asn Ile Lys Arg Trp Gln Ala
                165                 170                 175

Ile Tyr Lys Gln Phe Asp Thr Asp Arg Ser Gly Thr Ile Cys Ser Ser
                180                 185                 190

Glu Leu Pro Gly Ala Phe Glu Ala Ala Gly Phe His Leu Asn Glu His
                195                 200                 205

Leu Tyr Asn Met Ile Ile Arg Arg Tyr Ser Asp Glu Ser Gly Asn Met
 210                 215                 220

Asp Phe Asp Asn Phe Ile Ser Cys Leu Val Arg Leu Asp Ala Met Phe
 225                 230                 235                 240

Arg Ala Phe Lys Ser Leu Asp Lys Asp Gly Thr Gly Gln Ile Gln Val
                245                 250                 255

Asn Ile Gln Glu Trp Leu Gln Leu Thr Met Tyr Ser
                260                 265

(2) INFORMATION FOR SEQ ID NO:10:

(i) SEQUENCE CHARACTERISTICS:
         (A) LENGTH: 804 base pairs
         (B) TYPE: nucleic acid (C) STRANDEDNESS: double
        (D) TOPOLOGY: linear (ii) MOLECULE TYPE: cDNA (xi) SEQUENCE DESCRIPTION: SEQ ID NO:10:

| | | |
|---|---|---|
| ATGTTCCTGG TTAACTCGTT CTTGAAGGGC GGCGGCGGCG GCGGCGGGGG AGGCGGGGGC | 60 |
| CTGGGTGGGG GCCTGGGAAA TGTGCTTGGA GGCCTGATCA GCGGGGCCGG GGGCGGCGGC | 120 |
| GGCGGCGGCG GCGGCGGCGG CGGTGGTGGA GGCGGCGGTG GCGGTGGAAC GGCCATGCGC | 180 |
| ATCCTAGGCG GAGTCATCAG CGCCATCAGC GAGGCGGCTG CGCAGTACAA CCCGGAGCCC | 240 |
| CCGCCCCCAC GCACACATTA CTCCAACATT GAGGCCAACG AGAGTGAGGA GGTCCGGCAG | 300 |
| TTCCGGAGAC TCTTTGCCCA GCTGGCTGGA GATGACATGG AGGTCAGCGC CACAGAACTC | 360 |
| ATGAACATTC TCAATAAGGT TGTGACACGA CACCCTGATC TGAAGACTGA TGGTTTTGGC | 420 |
| ATTGACACAT GTCGCAGCAT GGTGGCCGTG ATGGATAGCG ACACCACAGG CAAGCTGGGC | 480 |
| TTTGAGGAAT TCAAGTACTT GTGGAACAAC ATCAAAAGGT GGCAGGCCAT ATACAAACAG | 540 |
| TTCGACACTG ACCGATCAGG GACCATTTGC AGTAGTGAAC TCCCAGGTGC CTTTGAGGCA | 600 |
| GCAGGGTTCC ACCTGAATGA GCATCTCTAT AACATGATCA TCCGACGCTA CTCAGATGAA | 660 |
| AGTGGGAACA TGGATTTTGA CAACTTCATC AGCTGCTTGG TCAGGCTGGA CGCCATGTTC | 720 |
| CGTGCCTTCA AATCTCTTGA CAAAGATGGC ACTGGACAAA TCCAGGTGAA CATCCAGGAG | 780 |
| TGGCTGCAGC TGACTATGTA TTCC | 804 |

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Synthetic DNA (xi) SEQUENCE DESCRIPTION: SEQ ID NO:11:

TCTGTGCGGG GTCTCTGCTG                                                    20

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Synthetic DNA (xi) SEQUENCE DESCRIPTION: SEQ ID NO:12:

GGAGTTGTGT CCCAGCCCTC A                                                  21

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Synthetic DNA (xi) SEQUENCE DESCRIPTION: SEQ ID NO:13:

| | |
|---|---|
| TTGTCCAGTT CTTCCTTCCG | 20 |

(2) INFORMATION FOR SEQ ID NO:14:

(i) SEQUENCE CHARACTERISTICS:
        (A) LENGTH: 517 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:14:

| | |
|---|---|
| GGAATTCAAG ACGCTCTGGC TGAAGATTCA GAAGTATCTG GAGCTCTATT GGGAAACTGA | 60 |
| TTATAACCAC TCGGGCACCA TCGATGCCCA CGAGATGAGG ACAGCCCTCA GGAAGGCAGG | 120 |
| TTTCACCCTC AACAGCCAGG TGCAGCAGAC CATTGCCCTG CGGTATGCGT GCAGCAAGCT | 180 |
| CGGCATCAAC TTTGACAGCT TCGTGGCTTG TATGATCCGC CTGGAGACCC TCTTCAAACT | 240 |
| ATTCAGCCTT CTGGACGAAG ACAAGGATGG CATGGTTCAG CTCTCTCTGG CCGAGTGGCT | 300 |
| GTGCTGCGTG TTGGTCTGAC CCGGGGTTTC GGACATCAGT GACACTCCCT GCCCCACTGC | 360 |
| TTGCTTCTTG TCACCCCTTC TCTACAATTT TGTGAACATT TATGCTCCAG TGGCATTCAC | 420 |
| TGGTTGTTCA TACCTTTCTT GCCCTGGGTC TATTTCAGCA GCACTGAGCT ATGAGCTATG | 480 |
| TAAGCCGACC CGGTGGGCCC AGTGGAGGGA AAGCAAT | 517 |

(2) INFORMATION FOR SEQ ID NO:15:

(i) SEQUENCE CHARACTERISTICS:
        (A) LENGTH: 664 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:15:

| | |
|---|---|
| TGTGGTGGTG CCCTCCACCT TCGAGCCCAA CAAGGAGGGC GACTTCGTGC TGCGCTTCTT | 60 |
| CTCAGAGAAG AGTGCTGGGA CTGTGGAGCT GGATGACCAG ATCCAGGCCA ATCTCCCCGA | 120 |
| TGAGCAAGTG CTCTCAGAAG AGGAGATTGA CGAGAACTTC AAGGCCCTCT TCAGGCAGCT | 180 |
| GGCAGGGGAG GACATGGAGA TCAGCGTGAA GGAGTTGCGG ACAATCCTCA ATAGGATCAT | 240 |
| CAGCAAACAC AAAGACCTGC GGACCAAGGG CTTCAGCCTA GAGTCGTGCC GCAGCATGGT | 300 |
| GAACCTCATG GATCGTGATG GCAATGGGAA GCTGGGCCTG GTGGAGTTCA ACATCCTGTG | 360 |
| GAACCGCATC CGGAATTACC TGTCCATCTT CCGGAAGTTT GACCTGGACA GTCGGGCAG | 420 |
| CATGAGTGCC TACGAGATGC GGATGGCCAT TGAGTCGGCA GGCTTCAAGC TCAACAAGAA | 480 |
| GCTGTACGAG CTCATCATCA CCCGCTACTC GGAGCCCGAC CTGGCGGTCG ACTTTGACAA | 540 |
| TTTCGTTTGC TGCCTGGTGC GGCTAGAGAC CATGTTCCGA TTTTTCAAAA CTCTGGACAC | 600 |
| AGATCTGGAT GGAGTTGTGA CCTTTGACTT GTTTAAGTGG TTGCAGCTGA CCATGTTTGC | 660 |
| ATGA | 664 |

(2) INFORMATION FOR SEQ ID NO:16:

(i) SEQUENCE CHARACTERISTICS:
        (A) LENGTH: 640 base pairs
        (B) TYPE: nucleic acid

```
        (C) STRANDEDNESS: double
        (D) TOPOLOGY: linear (ii) MOLECULE TYPE: cDNA (xi) SEQUENCE DESCRIPTION: SEQ ID NO:16:

ATGTTCCTGG TTAACTCGTT CTTGAAGGGC GGCGGCGGCG GCGGCGGGGG AGGCGGGGGC      60

CTGGGTGGGG GCCTGGGAAA TGTGCTTGGA GGCCTGATCA GCGGGGCCGG GGGCGGCGGC     120

GGCGGCGGCG GCGGCGGCGG CGGTGGTGGA GGCGGCGGTG GCGGTGGAAC GGCCATGCGC     180

ATCCTAGGCG GAGTCATCAG CGCCATCAGC GAGGCGGCTG CGCAGTACAA CCCGGAGCCC     240

CCGCCCCCAC GCACACATTA CTCCAACATT GAGGCCAACG AGAGTGAGGA GGTCCGGCAG     300

TTCCGGAGAC TCTTTGCCCA GCTGGCTGGA GATGACATGG AGGTCAGCGC CACAGAACTC     360

ATGAACATTC TCAATAAGGT TGTGACACGA CACCCTGATC TGAAGACTGA TGGTTTTGGC     420

ATTGACACAT GTCGCAGCAT GGTGGCCGTG ATGGATAGCG ACACCACAGG CAAGCTGGGC     480

TTTGAGGAAT TCAAGTACTT GTGGAACAAC ATCAAAAGGT GGCAGGCCAT ATACAAACAG     540

TTCGACACTG ACCGATCAGG GACCATTTGC AGTAGTGAAC TCCCAGGTGC CTTTGAGGCA     600

GCAGGGTTCC ACCTGAATGA GCATCTCTAT AACATGATCA                          640

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Synthetic DNA (xi) SEQUENCE DESCRIPTION: SEQ ID NO:17:

ATGGGATCCA AGCAAGAGCC CACGGCCA                                        28

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Synthetic DNA (xi) SEQUENCE DESCRIPTION: SEQ ID NO:18:

TGACTGCAGA AACCCCGGG TCAGAC                                           26
```